(12) United States Patent
Sharifi-Mehr et al.

(10) Patent No.: US 11,707,284 B2
(45) Date of Patent: Jul. 25, 2023

(54) BONE SCREWS, INSTRUMENTATION, AND METHODS OF USING OF SAME

(71) Applicant: K2M, Inc., Leesburg, VA (US)

(72) Inventors: Amir Ali Sharifi-Mehr, Bloomingdale, NJ (US); Oliver Buchert, Franklin Lakes, NJ (US); Shawn D. Stad, Lakeville, MA (US); Paul R. Rochette, Stanhope, NJ (US); Nicole Renee Fallacaro, Montvale, NJ (US); Lori Dombrowski, Elmwood Park, NJ (US); Mitch Baldwin, Grand Rapids, MI (US); Christopher P. Bell, New York, NY (US)

(73) Assignee: K2M, Inc., Leesburg, VA (US)

( * ) Notice: Subject to any disclaimer, the term of this patent is extended or adjusted under 35 U.S.C. 154(b) by 637 days.

(21) Appl. No.: 16/810,911

(22) Filed: Mar. 6, 2020

(65) Prior Publication Data

US 2020/0281608 A1    Sep. 10, 2020

Related U.S. Application Data

(60) Provisional application No. 62/814,505, filed on Mar. 6, 2019.

(51) Int. Cl.
*A61B 17/16* (2006.01)
*A61B 17/70* (2006.01)
(Continued)

(52) U.S. Cl.
CPC ...... *A61B 17/1617* (2013.01); *A61B 17/1631* (2013.01); *A61B 17/7032* (2013.01);
(Continued)

(58) Field of Classification Search
CPC ................................................ A61B 17/7082
See application file for complete search history.

(56) References Cited

U.S. PATENT DOCUMENTS

| 5,221,282 A | 6/1993 | Wuchinich |
| 5,788,699 A | 8/1998 | Bobst et al. |

(Continued)

OTHER PUBLICATIONS

Extended European Search Report for Application No. EP20161339.5, dated Sep. 24, 2020, pp. 1-3.
(Continued)

*Primary Examiner* — Andrew Yang
(74) *Attorney, Agent, or Firm* — Lerner David LLP

(57) ABSTRACT

A stylet control system for selectively advancing and retracting a stylet includes a stylet having a first end and a second end, the second end being threaded, a screwdriver defining a bore for receiving a portion of the stylet and having a screw-engaging end for engaging a screw, the stylet being rotationally fixed relative to the screwdriver. The system includes a control device having a passage for receiving the screwdriver and having an inner portion defining a lumen for receiving the portion of the stylet, the inner portion being threaded for engaging the threaded second end of the stylet, when the screwdriver is rotated in the first rotation direction and the control device is prevented from rotating, the screwdriver advances the screw in the first axial direction and the stylet retracts in a second axial direction, opposite the first axial direction.

20 Claims, 28 Drawing Sheets

(51) Int. Cl.
*A61B 17/86* (2006.01)
*A61B 17/00* (2006.01)

(52) U.S. Cl.
CPC ........ *A61B 17/7082* (2013.01); *A61B 17/864* (2013.01); *A61B 2017/00402* (2013.01)

(56) References Cited

U.S. PATENT DOCUMENTS

| | | | |
|---|---|---|---|
| 6,719,758 | B2 | 4/2004 | Beger et al. |
| 6,827,722 | B1 | 12/2004 | Schoenefeld |
| 7,207,995 | B1 | 4/2007 | Vandewalle |
| 7,819,905 | B2 | 10/2010 | Newcomb et al. |
| 8,366,719 | B2 | 2/2013 | Markey et al. |
| 8,715,293 | B2 | 5/2014 | Vandewalle |
| 9,156,145 | B2 | 10/2015 | Wang |
| 9,216,048 | B2 | 12/2015 | Markey et al. |
| 9,254,160 | B2 | 2/2016 | Pakzaban et al. |
| 9,433,445 | B2 | 9/2016 | Ramsay et al. |
| 9,855,087 | B2 | 1/2018 | Divincenzo et al. |
| 10,194,967 | B2 | 2/2019 | Baynham |
| 10,765,438 | B2 | 9/2020 | Kostrzewski |
| 2009/0275954 | A1 | 11/2009 | Phan et al. |
| 2009/0275993 | A1 | 11/2009 | Phan et al. |
| 2016/0135856 | A1 | 5/2016 | Ramsay et al. |
| 2018/0110553 | A1 | 4/2018 | DiVincenzo et al. |
| 2018/0325608 | A1* | 11/2018 | Kang ................ A61B 17/1671 |
| 2018/0368893 | A1* | 12/2018 | DiVincenzo ....... A61B 17/7082 |
| 2019/0125421 | A1 | 5/2019 | Smith et al. |

OTHER PUBLICATIONS

Cardoni, et al., Ultrasonic rock sampling using longitudinal-torsional vibrations, Physics Procedia, Jan. 2010, pp. 125-134, vol. 3, Science Direct, Elsevier.

DePuy Synthes, Viper Prime System, Surgical Technique, Apr. 2019, pp. 1-42, DePuy Synthes Spine.

Stryker, Sonopet Ultrasonic Aspirator, Product Catalog, 2016, pp. 1-20.

\* cited by examiner

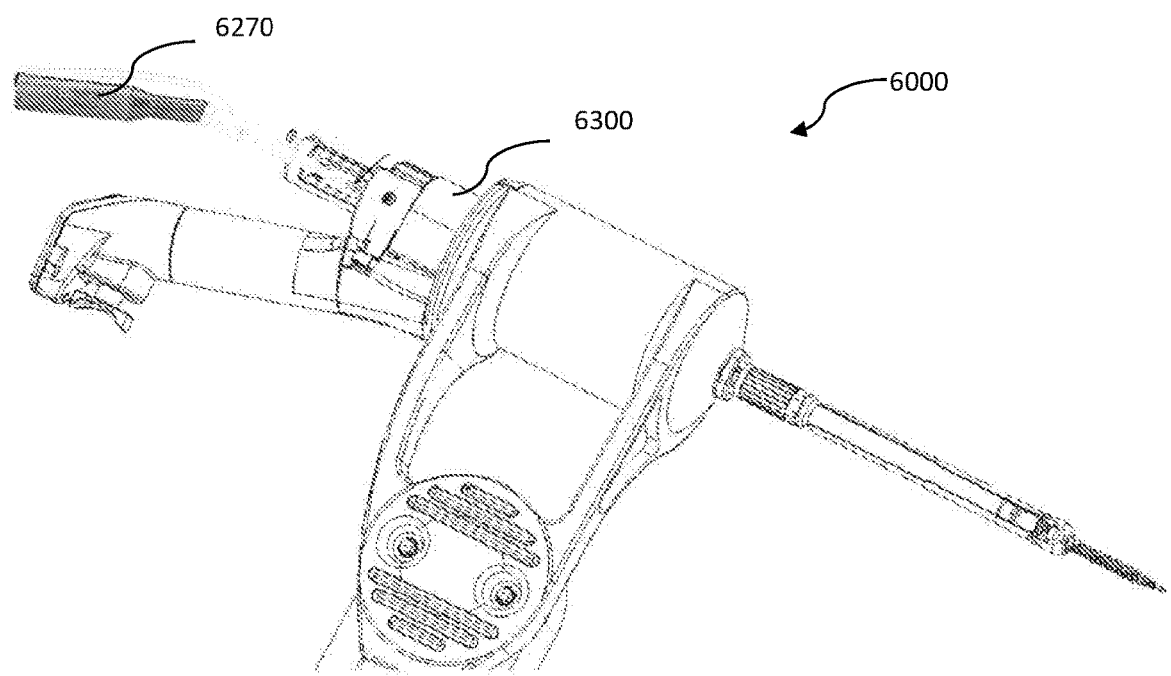
FIG. 59
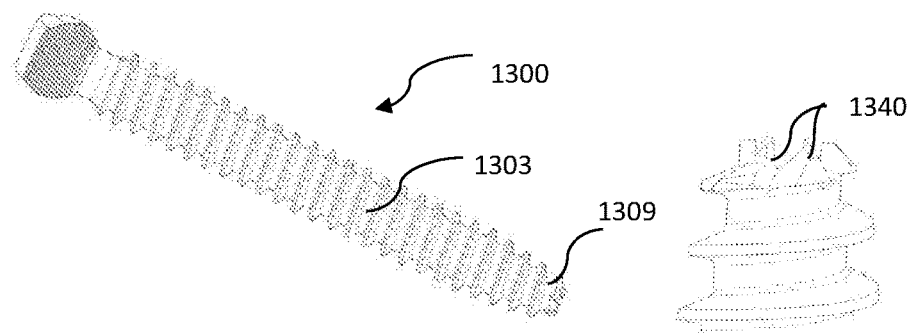 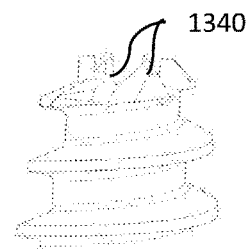
FIG. 60  FIG. 61
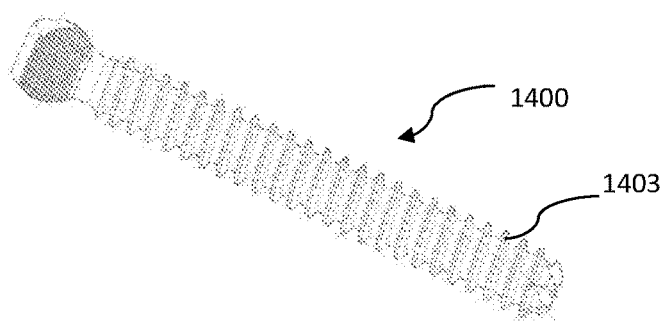 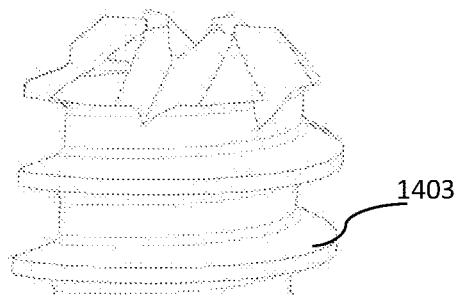
FIG. 62  FIG. 63

BONE SCREWS, INSTRUMENTATION, AND METHODS OF USING OF SAME

CROSS-REFERENCE TO RELATED APPLICATIONS

This application claims the benefit of the filing date of U.S. Provisional Patent Application No. 62/814,505 filed on Mar. 6, 2019, the disclosure of which is hereby incorporated by reference herein.

BACKGROUND OF THE INVENTION

The present invention generally relates to fixation devices, and more particularly, to spinal fasteners for single step insertion.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat many degenerative conditions and, in most cases, to relive pain suffered by the patient.

In some applications, a surgeon will install pedicle screws into the pedicles of adjacent vertebrae (along one or multiple levels of the spine) and thereafter connect the screws with a spinal rod in order to immobilize and stabilize the vertebral column Whether conducted in conjunction with interbody fusion or across single or multiple levels of the spine, the use of pedicle screws connected by fixation rods is an important treatment method employed by surgeons.

There remains room for improvement in the design and use of pedicle screws, particularly for surgical efficiency while maintaining safety and accuracy during screw insertion.

BRIEF SUMMARY OF THE INVENTION

According to an embodiment of the present disclosure, a method of spinal repair includes the steps of inserting a stylet through a lumen of a screw such that a distal tip of the stylet extends distally from a distal end of the screw, the stylet extending along an axis; advancing the screw and the stylet toward a bone until the distal tip of the stylet contacts the bone; and rotating the screw about the axis of the stylet in a first direction and simultaneously oscillating rotation of the stylet about the axis between the first direction and a second direction opposite to the first direction.

In other embodiments, the step of rotating may include advancing the screw into bone. The step of oscillating may include retracting the stylet away from the bone. When the screw is rotated in the first direction and the stylet is rotated in the second direction, the screw and the stylet may move in opposite directions along the axis. The method may include the step of removing the stylet from the bone. The screw may have a distal cutting edge. The method may include the step of inserting the stylet into the bone to a depth that is less than an intended insertion depth of the screw.

Another embodiment of the disclosure includes a system for spinal repair. The system includes a screwdriver that includes a drill adaptor that has an internal surface and is rotatable in a first direction and a second direction opposite the first direction. The screwdriver includes a gear system that has a driving gear, a driven gear, and one or more connector gears, the driving gear has a splined internal surface and an external surface configured to mate with the internal surface of the drill adaptor such that rotation of the drill adaptor causes rotation of the driving gear in the same direction. The driven gear has a splined internal surface, the driving gear and the driven gear are connected by the one or more connector gears such that rotation of the driving gear causes rotation of the driven gear in the opposite direction. The screwdriver includes a first ratchet pawl that has a splined outer surface configured to engage the splined inner surface of the driving gear and a second ratchet pawl that has a splined outer surface configured to engage the splined inner surface of the driven gear. The first and second ratchet pawls are splined in the same direction such that when one of the driving gear and the driven gear engages the respective first or second pawl, the other gear is disengaged from the respective first or second pawl. A shaft is connected to the first and second ratchet pawls. The system also includes a stylet that has a threaded portion and a housing surrounding the first and second ratchet pawls and rotationally locked relative to the shaft. The housing has a threaded inner surface to engage the threaded portion of the stylet.

In other embodiments, the first and second ratchet pawls may each connected to the shaft by a pin. The shaft may rotate in a single direction. Rotation of the drill adaptor may cause rotation of the stylet in the same direction as the drill adaptor. The threaded portion of the stylet may include threads having the same pitch as internal threads of the threaded portion of the housing. Rotation of the drill adaptor in the first direction about the axis may cause the stylet to remain axially fixed and rotation of the drill adaptor in the second direction about the axis may cause the stylet to retract axially. The system may include a fastener defining a lumen for receiving the stylet. Rotation of the drill adaptor in the first direction and the second direction about the axis may cause the bone screw to advance into the bone. The fastener may include a channel adapted to receive a spinal rod, a shaft extending from the head to a distal tip, the distal tip having at least one cutting edge.

Another embodiment of the present disclosure includes a fastener that includes a head which has a channel adapted to receive a spinal rod, and a shaft extending from the head to a distal tip. The shaft has a thread, and the distal tip has at least one cutting edge.

In other embodiments, the fastener may be cannulated. The threads may continuously transition into the at least one cutting edge. The threads may terminate at a location spaced apart from the at least one cutting edge.

Yet another embodiment of the present disclosure includes a stylet control system for selectively advancing and retracting a stylet that includes a stylet that has a first end and a second end. The second end is threaded. The system includes a screwdriver that defines a bore for receiving the stylet and has a screw-engaging end for engaging a screw, the stylet is rotationally fixed relative to the screwdriver. The system includes a control device that is attachable to the screwdriver and has an inner surface defining a lumen for receiving the stylet. A portion of the inner surface is threaded for engaging the threaded second end of the stylet. When the control device is rotated in a first rotation direction and the screwdriver is prevented from rotating, the stylet advances in a first axial direction, and when the screwdriver is rotated in the first rotation direction and the control device is prevented from rotating, the screwdriver advances the screw in the first axial direction and the stylet retracts in a second axial direction, opposite the first axial direction.

In other embodiments, the threaded portion of the stylet may be an integral and monolithic part of the stylet. The stylet may be keyed and the screwdriver includes a corresponding keyed feature such as a hex feature on an inner surface to rotatably lock the stylet to the screwdriver. The system may include a quick connect feature to couple the control device to the screwdriver. The control device and the screwdriver may each include a robotic end effector.

Yet another embodiment of the present disclosure includes a stylet control system for selectively advancing and retracting a stylet that includes a stylet that has a first end and a second end. The second end is threaded. The system includes a screwdriver that defines a bore for receiving a portion of the stylet and has a screw-engaging end for engaging a screw, the stylet is rotationally fixed relative to the screwdriver. The system includes a control device that is operatively connected to the screwdriver and has an inner portion defining a lumen for receiving the portion of the stylet. The inner portion is threaded for engaging the threaded second end of the stylet. When the screwdriver is rotated in the first rotation direction and the control device is prevented from rotating, the screwdriver advances the screw in the first axial direction and the stylet retracts in a second axial direction, opposite the first axial direction.

In other embodiments, the stylet may be keyed and the screwdriver includes a corresponding keyed feature such as a hex feature on an inner surface to rotatably lock the stylet to the screwdriver. The system may include a robotic end effector and a cap to couple the screwdriver to the robotic end effector. The control device may be operatively connected to a robotic end effector. The control device may include an ultrasonic transducer for imparting an ultrasonic force to the stylet. The ultrasonic transducer may be positioned within a housing of the control device. The ultrasonic transducer may be detachable from and external to a housing of the control device. The ultrasonic transducer may include piezoelectric material. The inner portion of the control device may include at least one threaded pawl for engagement with the threads of the stylet. The system may be part of a kit which includes a robotic end effector. The kit may include a bone screw attachable to the screwdriver. The bone screw may be self-drilling. The bone screw may be cannulated. The control system of the kit may include an ultrasonic transducer for imparting an ultrasonic force to the stylet.

Yet another embodiment of the present disclosure includes a stylet control system for selectively advancing and retracting a stylet including a stylet having a first end and a second end, a screwdriver defining a bore for receiving the stylet and having a screw-engaging end for engaging a screw, the stylet being rotationally fixed relative to the screwdriver, robotic end effector having a passage therethrough, a cap configured to be received within a portion of the passage of the robotic end effector and being operatively connected to the screwdriver, a retraction feeder receivable within a lumen of the cap and having a mating engagement member for engaging the engagement member of the stylet, when the screwdriver is rotated in a first rotation direction, the screwdriver advances the screw in the first axial direction and the stylet engages the engagement member of the retraction feeder to retract the stylet in a second axial direction, opposite the first axial direction.

In other embodiments, the engagement members of the stylet and retraction feeders may include mating threads, and the retraction feeder includes a threaded pawl for one-way engagement of the threaded stylet. The stylet may be keyed and the screwdriver may include a corresponding keyed feature such as a hex feature on an inner surface to rotatably lock the stylet to the screwdriver. The control system may further include an ultrasonic transducer for imparting an ultrasonic force to the stylet. The retraction feeder may be rotatably locked within the end effector.

Another embodiment of the present disclosure includes a stylet control system for selectively advancing and retracting a stylet including a stylet having a first end and a second end, the second end being threaded, a screwdriver defining a bore for receiving the stylet and having a screw-engaging end for engaging a screw, the stylet being rotationally fixed relative to the screwdriver, a robotic end effector having a passage therethrough, a cap configured to be received within a portion of the passage of the robotic end effector and being operatively connected to the screwdriver, and a retraction feeder receivable within a lumen of the cap and having a threaded pawl for one-way engagement with the threads of the second end of the stylet, when the screwdriver is rotated in a first rotation direction, the screwdriver advances the screw in the first axial direction and the threads of the stylet engages the threaded pawl of the retraction member to retract the stylet in a second axial direction, opposite the first axial direction.

BRIEF DESCRIPTION OF THE DRAWINGS

FIG. 59 is a perspective side view of a robotically operative stylet control device in conjunction with a ultrasonic transducer;

FIG. 60 is a perspective view of a fastener in accordance with another aspect of the present disclosure;

FIG. 61 is an enlarged view of the distal end of the fastener of FIG. 60;

FIG. 62 is a perspective view of a fastener in accordance with another aspect of the present disclosure;

FIG. 63 is an enlarged view of the distal end of the fastener of FIG. 62;

DETAILED DESCRIPTION

The present invention generally relates to a fastener to be used in conjunction with spinal rods during spinal surgery. Those of skill in the art will recognize that the following description is merely illustrative of the principles of the invention, which may be applied in various ways to provide many different alternative embodiments.

The various embodiments of the bone screws or fasteners described below are designed to facilitate efficient and accurate screw insertion during surgery. In some embodiments, the fasteners are cannulated for receiving a stylet extending through the length of the channel. In such cases, the stylet includes a sharp tip to create a pilot hole. In other embodiments, certain fasteners are solid along the shaft rather than being cannulated. In such embodiments, the distal tip of the shaft of the fastener includes a sharp cutting tip for forming a pilot hole and drilling into the bone. The use of the fasteners and/or stylet for creating the pilot hole and cutting into the bone until the threads of the fasteners engage and pull the screw into the bone eliminates the steps of reaming, awling, tapping the hole, or otherwise preparing the hole, before the screw can be placed into the prepared hole. As a result, the fasteners in the present disclosure provide for more efficient implantation.

Figure 1:
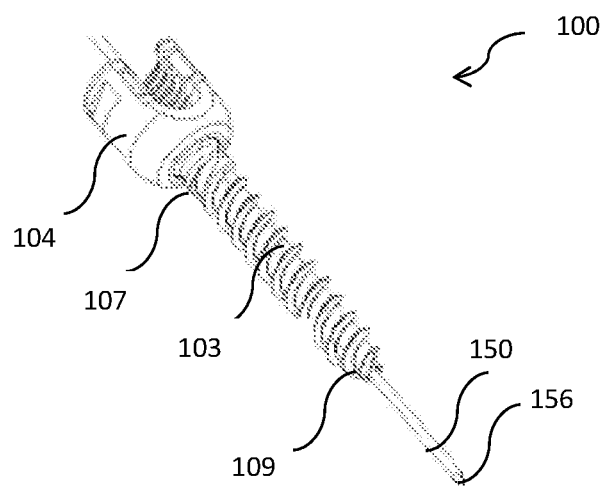
FIG. 1 is a perspective view of a fastener and stylet in accordance with a first embodiment of the present disclosure.
Figure 2:
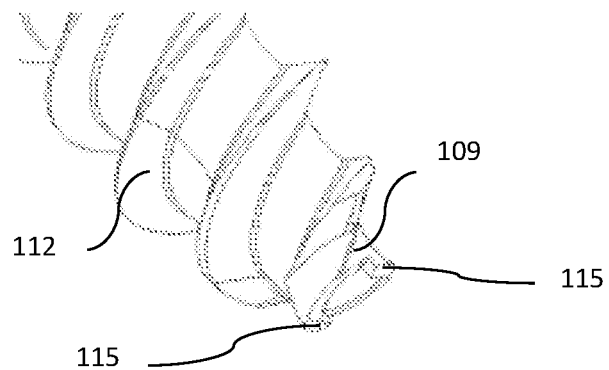
FIG. 2 is an enlarged perspective view of the distal end of the fastener of FIG. 1.

FIGS. 1-2 depict a first embodiment of a fastener 100 and a Kirschner wire or stylet 150 that is configured for spinal applications, and in particular, for the use of fastener 100 as a pedicle screw, as will be described in detail below. Fastener 100 includes a screw shaft 103 and a tulip 104, which has a channel adapted to receive a spinal rod. A spinal rod can be installed into tulip 104 and held in place by a set screw (not shown), which can be threaded into internal threads of tulip 104.

Fastener 100 is polyaxial in that shaft 103 is separate from and polyaxially movable with respect to tulip 104. Tulip 104 and a proximal end 107 of shaft 103 can generally be referred to as a head of fastener 100. Shaft 103 extends along a longitudinal axis from its proximal end 107 to a distal tip 109. Proximal end 107 of shaft 103 forms an interference fit connection with a distal opening of tulip 104 to create the polyaxial connection. Tulip 104 can swivel to form different angles with respect to shaft 103 which allows for proper rod placement. In alternative embodiments, the fastener may be a monolithic structure with the tulip statically connected with the proximal end of shaft 103.

Shaft 103 includes threads 112 extending between proximal end 107 and distal tip 109. As seen in FIGS. 1 and 2, fastener 100, including shaft 103 and tulip 104, is cannulated through its entire length for receiving stylet 150 as shown. Stylet 150 terminates at a sharp distal point 156.

With reference to FIG. 2, distal tip 109 of shaft 103 is an annular surface that includes at least one cutting edge 115 for cutting into the cortical bone and facilitating initial engagement with the bone during insertion of fastener 100 such that distal tip 109 may be referred to as a drill tip. Cutting edges 115 are shaped to propagate a hole in the bone during advancement of fastener 100. The annular surface of distal tip 109 forms two flat surfaces between cutting edges 115 in the form of notches for cutting the bone.

Threads 112 extend along shaft 103 to a distal end 112*a* adjacent the distal tip 109 and cutting edges 115. With the placement of thread 112 in close proximity to the cutting edges 115, the threading facilitates the pulling motion of fastener 100 into the bone immediately after cutting edges penetrate cortical bone.

Figure 3:
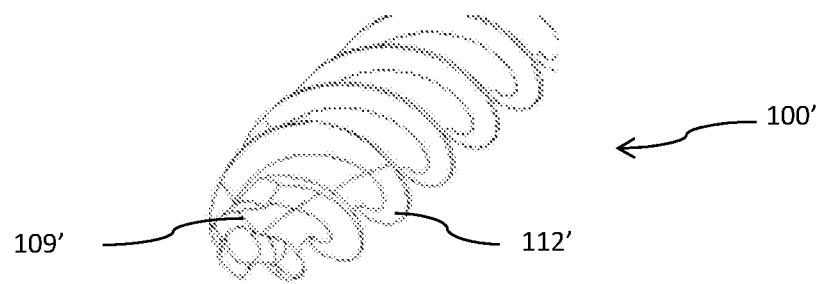
FIGS. 3 and 4 are enlarged perspective views of an alternative embodiment according to another embodiment of the present disclosure.
Figure 4:
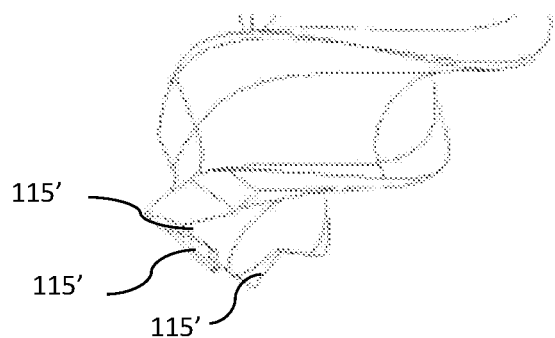

The embodiment of fastener 100 shown in FIGS. 1 and 2 includes a double lead thread. With a double lead thread, there are, as shown, two cutting edges 115. Other embodiments may include a single or a triple lead thread, or may include more threads around shaft 103. For example, FIGS. 3 and 4 show a fastener 100' which is substantially similar to fastener 100 except that the threading includes a triple lead thread, and fastener 100' includes three cutting edges 115' at distal tip 109' for cutting into the cortical bone until threads 112' engage the bone and pull fastener 100' into placement. The cutting edges 115' are formed by the thread exiting the bottom of the screw tip. A triple lead thread advantageously provides a more balanced approach that prevents grabbing of the bone by only one of the cutting edges. The number of cutting edges 115 does not have to equal the number of threads 112 along shaft 103, since the function of cutting edges 115 to penetrate the bone is not always aligned with the function of threads 112 to advance fastener 100 along its trajectory within the bone.

Figure 5:
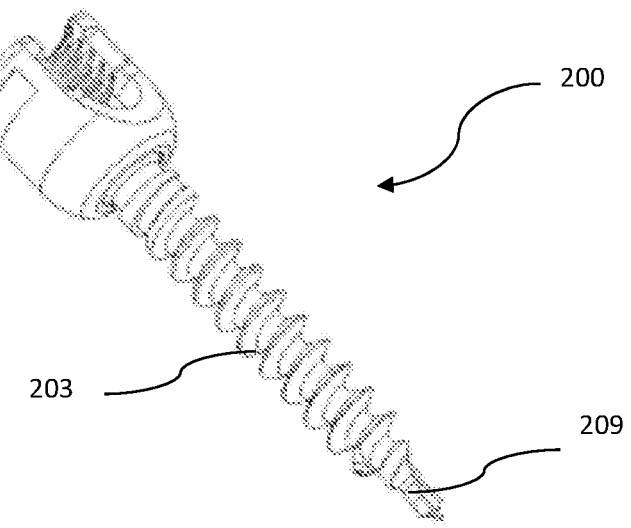
FIG. 5 is a perspective view of a fastener in accordance with another embodiment of the present disclosure.
Figure 6:
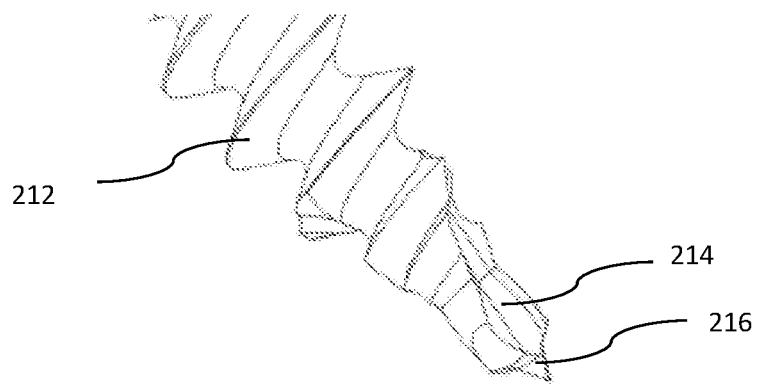
FIG. 6 is an enlarged perspective view of the distal end of the fastener of FIG. 5.

FIGS. 5 and 6 depict a fastener 200 according to another embodiment of the present disclosure. Fastener 200 differs from fastener 100 in that shaft 203 is not cannulated but rather includes a cutting drill point 216 at the distal end 209 of the shaft. Threads 212 transition into the cutting point 216 at distal end 209, such that cutting point 216 forms the drill tip to cut into the bone to form the hole without the use of a stylet. The distal portion of the shaft 203 may include one or more flutes 214. Fastener 200 is polyaxial, though it can also be constructed as a monoaxial embodiment.

The fasteners of FIGS. 3-6 include a smooth transition region between the cutting features and the threads. The smooth transition region allows the cutting features to continuously cut into bone until the cutting blends into the threads, which create the axial force to push the threads forward into the bone. In FIG. 4 the geometry is similar to an end mill, and in FIG. 5 the geometry is similar to a brad point drill tip.

As a result of cutting drill point 216, fastener 200 can be inserted into the bone in one step which eliminates a separate step of reaming or drilling the hole with a separate tool before inserting fastener 200 into the bone. This advantageously reduces the number of steps and tools required during surgery. Additionally, the sharp cutting point 216 facilitates accuracy of the placement of the bone screw during insertion because it can be pushed into the bone to penetrate slightly and dock fastener 200 to prevent skiving during insertion.

Figure 7:
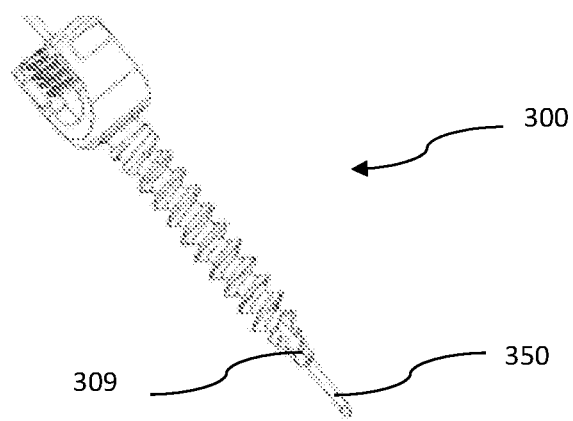
FIG. 7 is a perspective view of a fastener and stylet in accordance with another aspect of the present disclosure.
Figure 8:
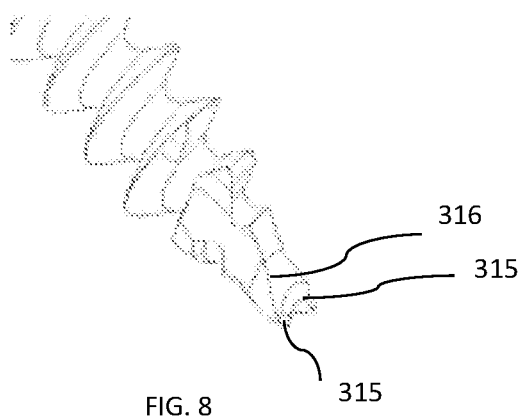
FIG. 8 is an enlarged view of the distal end of the fastener of FIG. 7.

FIGS. 7 and 8 depict a fastener 300 similar to fasteners 100 and 200. Like fastener 100, fastener 300 is cannulated for receiving stylet 350. Fastener 300 includes distal end 309 formed into a drill point 316 with two cutting edges 315. Drill point 316 is sized and configured to cut into the bone to form the hole during insertion of fastener 300 into a pedicle. As with fastener 100, stylet 350 can be pushed into the bone to prevent skiving of fastener 300 during insertion.

Figure 9:
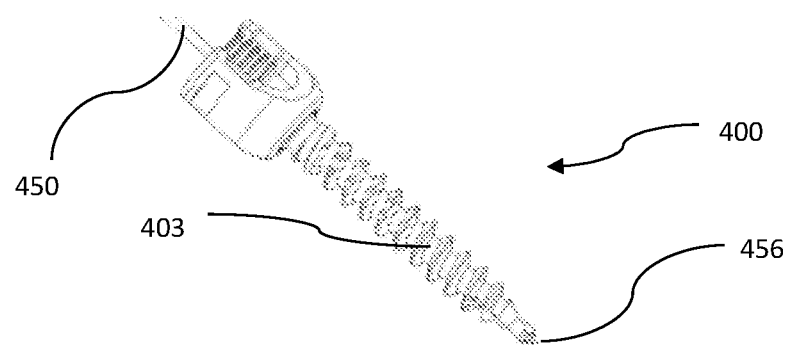
FIG. 9 is a perspective view of a fastener and stylet in accordance with yet another aspect of the present disclosure.
Figure 10:
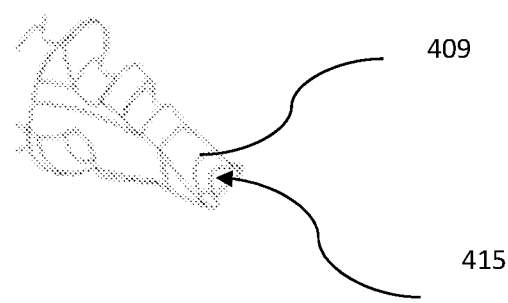
FIG. 10 is an enlarged view of the distal end of the fastener of FIG. 9.
Figure 11:
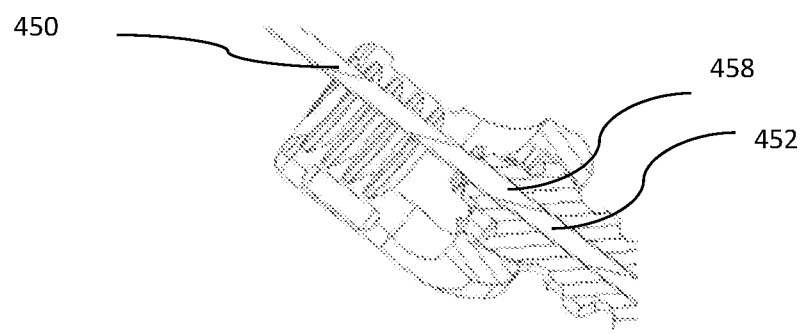
FIG. 11 is a cross-sectional view of the proximal end of the fastener in conjunction with the Stylet of FIG. 9.

Another embodiment of the present disclosure is a fastener 400, shown in FIGS. 9-11. Fastener 400 includes channel 415 extending through the entirety of the shaft 403 for receiving stylet 450.

Stylet 450 includes elongated shaft body 452 extending along a longitudinal axis and terminating at sharp distal tip 456. Body 452 of stylet 450 extends through a proximal end of the shaft 403 and out of distal end 409 such that the sharp tip 456 of stylet 450 extends beyond the distal end 409 of the shaft 403 of fastener 400.

Body 452 of stylet 450 includes a keyed stop 458 that is engageable with a corresponding stop member, ledge, or shoulder positioned on or near a proximal end of shaft 403. In an engaged position, the stylet is rotationally and axially fixed with respect to shaft 403 of fastener 400. Stylet 450 can be disengaged from the locked relationship between the stylet and the shaft 403 so that the stylet can be removed from the cannulated channel of the fastener. Alternatively, stylet 450 may be frangibly connected to the screw, such that the frangible connection can be fractured for removal of the stylet after the bone screw is inserted into bone.

Keyed stop 458 may be in the form of a flat section running along at least a length of body 452 of stylet 450 to ensure that the body remains in an axially-fixed and rotatably-fixed position relative to shaft 403. The cross-section of stylet 450 is non-circular to include the flat section or to be hexagonally shaped so that it can be rotationally locked with the internal lumen of fastener 400. Thus, once stylet 450 is in place, the tip 456 coupled with distal end 409 of fastener 400 is configured similarly to cutting point 216 of non-cannulated fastener 200.

During use, stylet 450 is first positioned within channel 415 of shaft 403 such that the keyed stop is engaged and the stylet is axially and rotationally fixed relative to the shaft. With the stylet 450 secured to the shaft 403, the sharp tip 456 of the stylet 450 extends further distally than the fastener to form the cutting point. With stylet 450 secured to shaft 403, distal end 409 of fastener 400 has the same shape and geometry of fastener 200. Fastener 400 and stylet 450 rotate simultaneously as the fastener and stylet are advanced into bone. After fastener 400 is implanted to the desired depth in the bone, the keyed stop is disengaged and stylet 450 can be removed from the fastener. The removal of stylet 450 may be advantageous in certain instances because the sharp point 456 of the stylet is removed from the anatomy which may result in less damage to the surround area over time.

Figure 12:
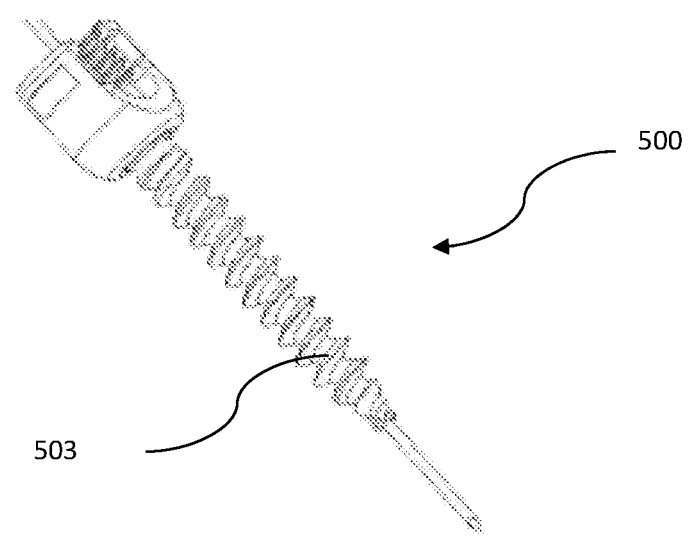
FIG. 12 is a perspective view of another fastener in conjunction with a stylet according to another embodiment of the present disclosure.
Figure 13:
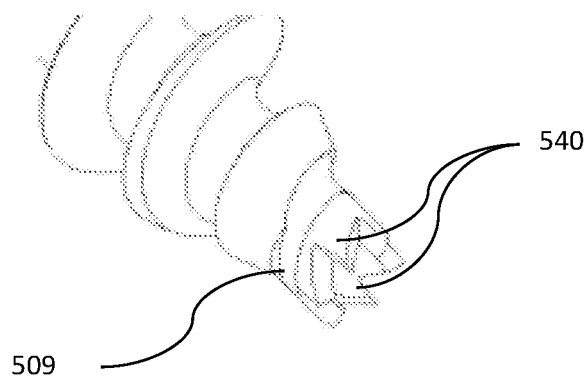
FIG. 13 is an enlarged perspective view of the distal end of the fastener of FIG. 12.

FIGS. 12 and 13 depict a fastener 500 according to yet another embodiment of the present disclosure. Fastener 500 includes a cannulated threaded shaft 503 that terminates at distal tip 509. Distal tip 509 includes saw tooth members 540 positioned around the circumference thereof. Each saw tooth member 540 is in the shape of a triangular member terminating in a point. In the illustrated embodiment, there are six saw tooth members 540; however, in other embodiments there may be more or less of the saw tooth members positioned around the circumference of the distal tip. Additionally, the saw tooth members may be larger or smaller depending on the number of members around the circumference. Although shown as triangularly shaped, in other examples, the saw tooth members may be trapezoidal, rectangular, etc.

Figure 14:
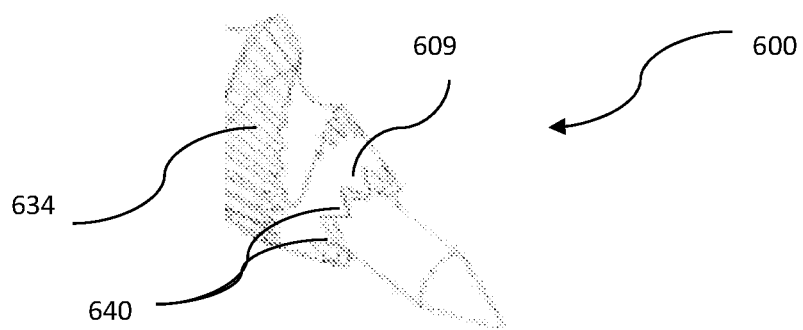
FIG. 14 is an enlarged view of a distal end of an alternative fastener according to another embodiment of the present disclosure.

FIG. 14 depicts a fastener 600 according to another embodiment of the present disclosure. Fastener 600 includes cannulated shaft that includes thread having serrations 634 along a portion of the shaft. Serrations 634 include alternating peaks and valleys. Serrations 634 may be in the form of the various embodiments of serrations described in U.S. application Ser. No. 15/645,264 filed on Jul. 10, 2017 and titled Spinal Fastener with Serrated Thread. The inclusion of the serrations reduces insertion torque, which reduces the chance of bone fracture and breaching. The shaft terminates at distal tip 609 which includes sharp triangular-shaped saw tooth members 640 positioned around the circumference of the distal tip.

FIGS. 60-61 show a fastener 1300 according to another embodiment of the present disclosure. Fastener 1300 includes cannulated shaft 1303 that is threaded along its length to distal tip 1309. Shaft 1303 tapers toward distal tip 1309, and distal tip 1309 includes substantially V-shaped saw tooth members 1340 positioned around the circumference of the distal tip 1309, as best shown in FIG. 61.

FIGS. 62-63 show fastener 1400 according to another embodiment of the present disclosure. Fastener 1400 is similar in most respects to fastener 1300 except that shaft 1403 has a constant major diameter.

Figure 64:
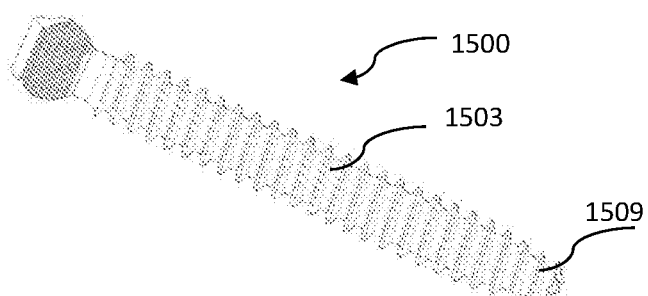
FIG. 64 is a perspective view of a fastener in accordance with another aspect of the present disclosure.
Figure 65:
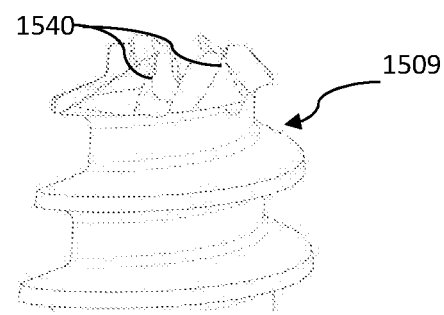
FIG. 65 is an enlarged view of the distal end of the fastener of FIG. 64.
Figure 66:
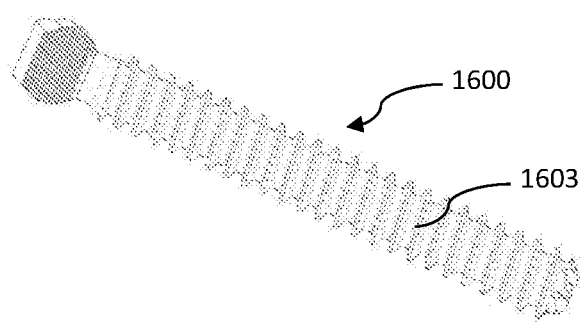
FIG. 66 is a perspective view of a fastener in accordance with another aspect of the present disclosure.
Figure 67:
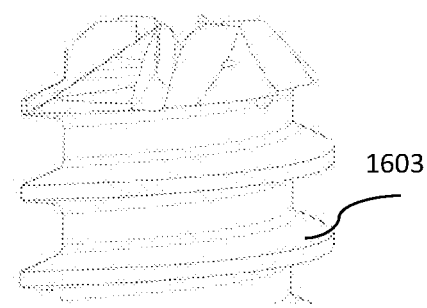
FIG. 67 is an enlarged view of the distal end of the fastener of FIG. 66.
Figure 68:
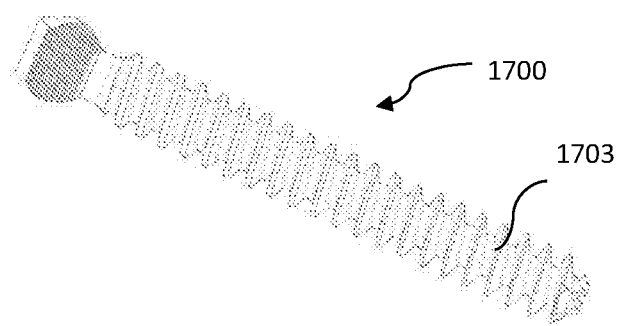
FIG. 68 is a perspective view of a fastener in accordance with another aspect of the present disclosure.
Figure 69:
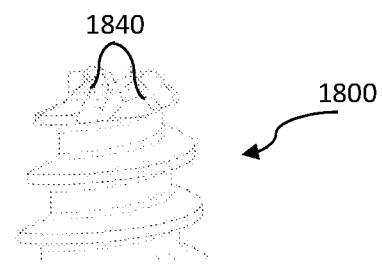
FIG. 69 is an enlarged view of a distal end of a fastener according to another aspect of the present disclosure.

FIGS. 64-65 show fastener 1500 according to another embodiment of the present disclosure. Fastener 1500 includes cannulated shaft 1503 which tapers to distal tip 1509. Fastener 1500 includes substantially C-shaped saw tooth members 1540 such that between adjacent tooth members is a curved edge rather than the pointed edge shown in FIG. 61 in connection with fastener 1300. FIGS. 66-67 show fastener 1600 according an embodiment that is substantially identical to fastener 1500 except that fastener 1600 includes shaft 1603 with major constant diameter rather than a tapering profile, as in fastener 1500. FIG. 68 shows fastener 1700 which is another variant of fasteners 1500 and 1600, with fastener 1700 including shaft 1703 with a constant major diameter and tapering minor diameter. FIG. 69 shows the distal tip of fastener 1800, which is another variant to fastener 1500. Fastener 1800 includes saw tooth members 1840 angled relative to one another.

Figure 70:
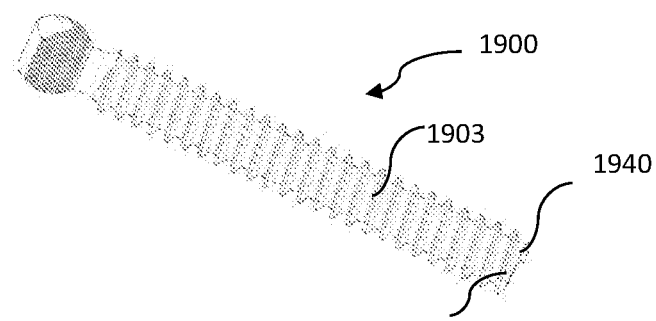
FIG. 70 is a perspective view of a fastener in accordance with another aspect of the present disclosure.

FIG. 70 shows fastener 1900 according to another embodiment of the present disclosure. Fastener 1900 includes cannulated threaded shaft 1903 which terminates at distal tip 1909. Distal tip 1909 includes a only single cutting member 1940 for cutting into the bone. The single cutting member 1940 may have a rectangular, trapezoidal, triangular, or c-shape.

Figure 15:
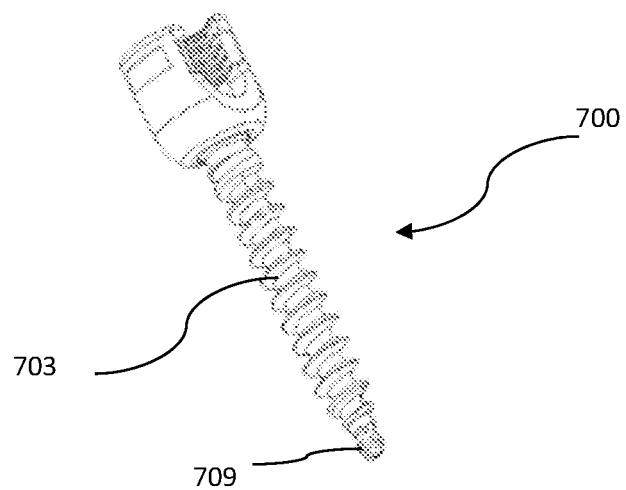
FIG. 15 is a perspective view of a fastener according to yet another embodiment of the present disclosure.
Figure 16:
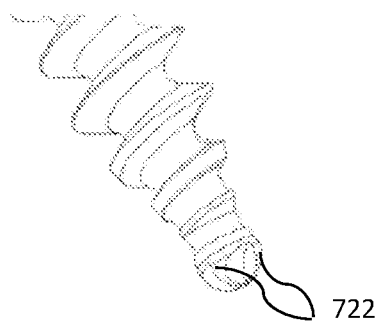
FIG. 16 is an enlarged view of the distal end of the fastener of FIG. 15.

Referring to FIGS. 15 and 16, a fastener 700 includes a non-cannulated threaded shaft 703 terminating at rounded distal tip 709 that includes burr members 722 that allow for high speed cutting of the cortical bone. The burr members 722 are positioned around the circumference of the distal tip and are separated from one another by cut-out portions.

Figure 17:
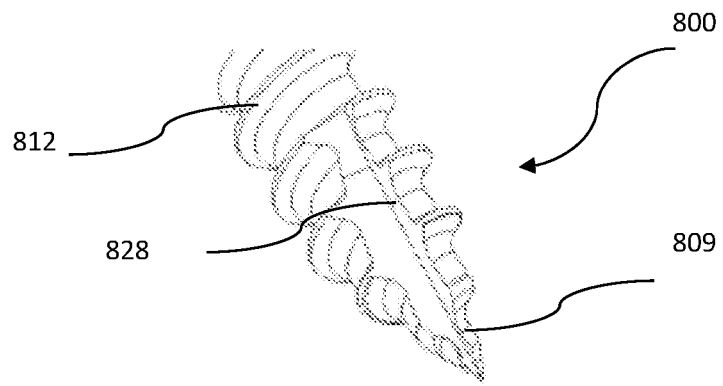
FIG. 17-21 are enlarged perspective views of the distal ends of fasteners according to various alternative embodiments of the present disclosure.

In another embodiment, shown in FIG. 17, a fastener 800 includes a self-drilling distal tip 809 with one or more flutes 828 positioned at a distal portion of shaft 803. Threading 812 extends to the distal tip 809 which allows the shaft to engage and anchor into the bone immediately upon contact.

Figure 18:
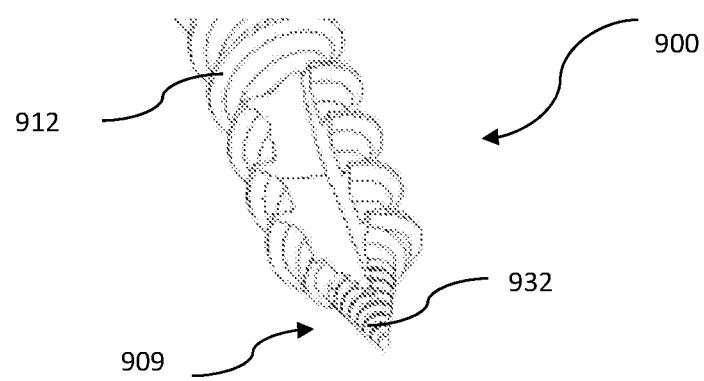

In an alternative embodiment, shown in FIG. 18, a fastener 900 includes self-drilling distal tip 909 of the shaft which includes a helically threaded portion 932. The pitch of threaded portion 932 is less than that of threads 912 of the shaft. As shown in the illustrated embodiment, the distal end of the shaft may include one or more flutes that do not cut across the entire helically threaded portion 932.

Figure 19:
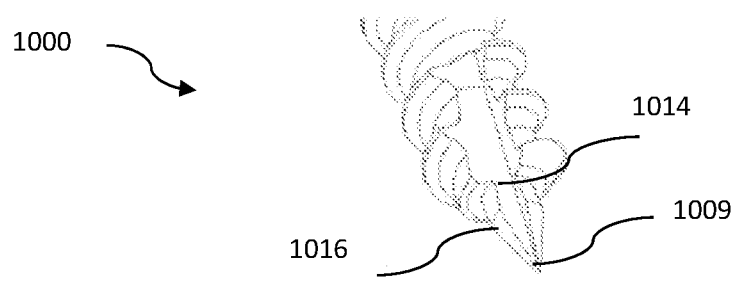

In yet another embodiment, FIG. 19 shows a fastener 1000 having a distal tip that includes first threaded portion 1014 and second unthreaded portion 1016 which tapers inwardly to form a pointed tip 1009 to facilitate a self-drilling tip. The shaft also includes a cutting flute extending to pointed tip 1009.

Figure 20:
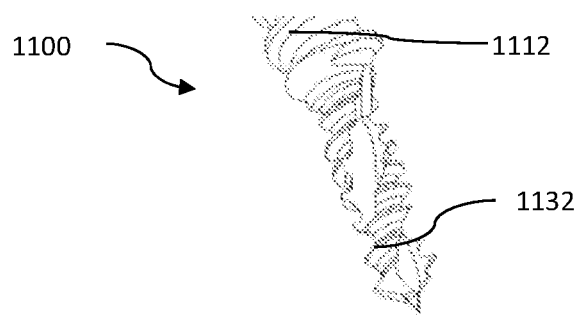

FIG. 20 shows a fastener 1100 which includes a threaded portion 1112 adjacent a distal portion of the shaft that has tap threads 1132. Tap threads 1132 extend along less than half of the length of the shaft and may extend along about one-third of the length of the shaft. Tap threads 1132 are of a smaller pitch than the threads of threaded portion 1112, and also include a helical flute extending along tap threads 1132 to facilitate threading of the hole through the cortical bone.

Figure 21:
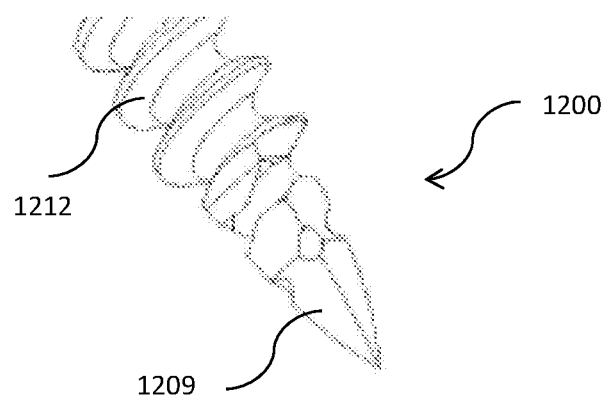

In another embodiment, shown in FIG. 21, a fastener 1200 includes a shaft that terminates at awl tip 1209. Awl tip 1209 is configured to create the pilot hole during implantation of fastener 1200. Threads 1212 may overlap a portion of the awl tip or, as shown, threads 1212 may terminate at the proximal-most end of the awl tip.

It is contemplated that each of the non-cannulated fasteners can alternatively be cannulated for use with a stylet.

Figure 22:
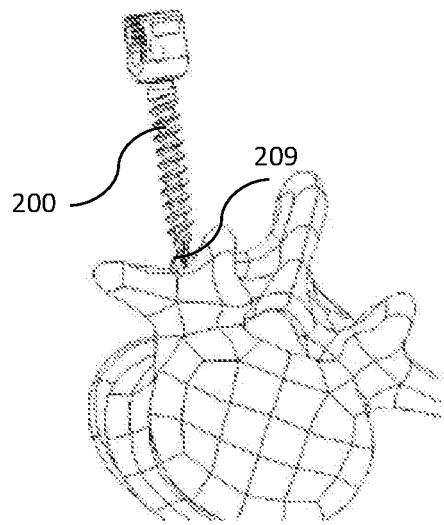
FIGS. 22-23 are schematic representations of the fastener of FIG. 3 during implantation into a pedicle bone.
Figure 23:
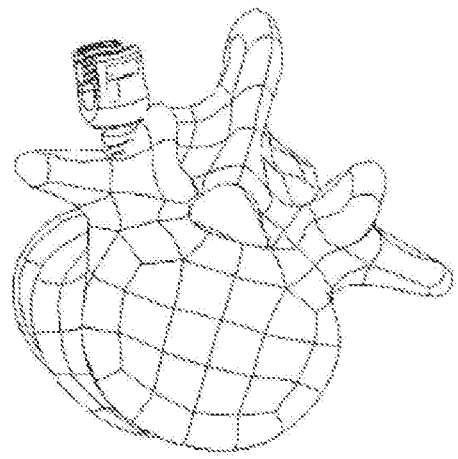

The method of using the solid, non-cannulated fasteners (i.e. fasteners 200, 700, 800, 900, 1000, 1100, 1200) will now be described with specific reference to fastener 200, although the method applies to each of the aforementioned non-cannulated fasteners. As shown in FIG. 22, fastener 200 is positioned on the pedicle bone and distal tip 209 is docked onto the bone. The fastener 200 is pushed into the bone until the distal tip penetrates the bone to dock the fastener. This allows for an accurate point of entry during initial insertion of the fastener into the bone and prevents skiving of the screw. Torque is applied to the fastener, either by manual insertion, robotic or power insertion. The distal tip 209 cuts the bone until threads 212 catch bone and advance the screw into the bone, shown in FIG. 23.

A similar method of implantation is used with fastener 400 as the stylet 450 and fastener become "integral" with one another while stylet 450 is in the engaged position and axially and rotationally locked with respect to fastener 400. After implantation of fastener 400, stylet 450 is removed from the bone.

Figure 24:
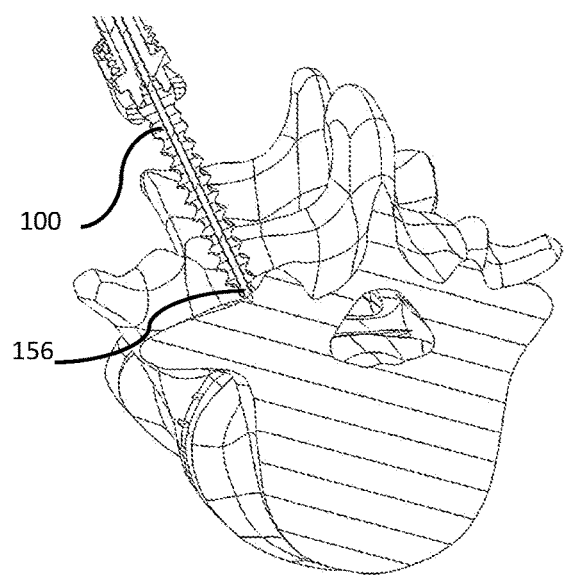
FIGS. 24-27 are schematic representations of the fastener of FIG. 1 during implantation into a pedicle bone.
Figure 25:
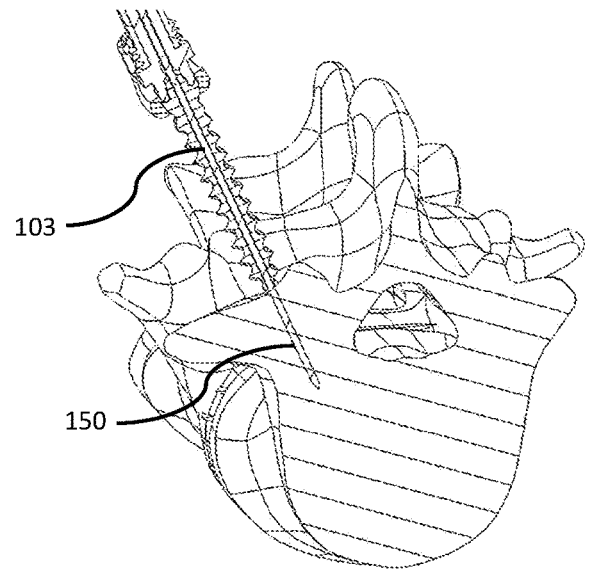
Figure 26:
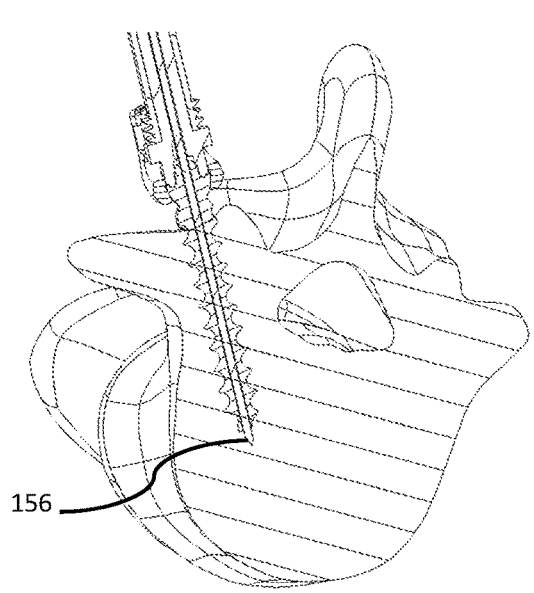
Figure 27:
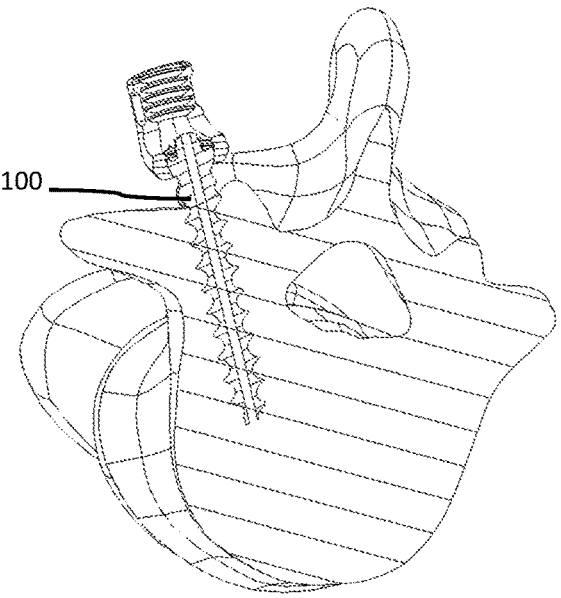

The method of using the cannulated fasteners (i.e. fasteners 100, 300, 500, 600) will now be described with specific reference to fastener 100, although the method applies to each of the aforementioned cannulated fasteners. As shown in FIG. 24, stylet 150 is positioned within the channel of the shaft 103 of fastener 100. Sharp tip 156 of stylet 150 is used to form the pilot hole. The stylet is then advanced into the bone, while shaft 103 remains placed on or above the bone surface. The stylet is advanced into bone about 5 to 30 millimeters, as shown in FIG. 25. Torsion is applied to fastener 100 such that the screw rotates with respect to stylet 150, which remains at its same depth within the bone during insertion of fastener 100, and the cutting feature of the distal end of fastener 100 cuts into the cortical bone. For fastener 100, the cutting feature includes cutting edges 115. As fastener 100 cuts into bone, stylet 150 remains axially fixed and does not advance farther into the bone. The securement of stylet 150 in the bone at the desired depth of screw placement while fastener 100 is being advanced into the bone helps to prevent skiving. The advancement of fastener 100 relative to the secured stylet 150 helps to maintain the accurate trajectory of the fastener. Fastener 100 is advanced to the desired depth by continuing to rotate fastener 100 until its threads engage the bone and advance fastener 100 down stylet 150, as shown in FIG. 26. The depth to which fastener 100 is inserted is just smaller than the depth to which stylet 150 has been inserted. After final placement of the fastener, stylet 150 is pulled proximally and removed from the shaft of fastener 100, as shown in FIG. 27. Removal of the sharp tip of stylet 150 is advantageous in that it prevents damage that could otherwise be caused by the sharp feature to the surrounding area after the procedure.

The use of the stylet to maintain the proper trajectory during screw placement is advantageous particularly in instances where a fastener is screwed into a first surface of a first bone, is passed out of a second surface of the first bone, is made to traverse a gap between bone segments, and is screwed into a second bone segment. Typically, without the use of a stylet, as the screw exits the first bone and traverses the gap, the screw's path loses its accuracy before entering the second bone. In the present disclosure, the movement of the screw over the previously positioned and secured stylet maintains the placement of the screw along the proper position of the second bone despite having to traverse a gap. This technique is particularly useful in surgeries involving smaller pedicles, such as the pedicles of the thoracic spine. Placement of the stylet through the bone portions across the gap does not present the same difficulties, particularly given its sharp tip and the fact that it can be pushed or oscillated during insertion as opposed to being rotated. Often the skiving of a bone screw occurs based on the tip of the screw moving along the bone surface as it attempts to penetrate the surface while it is rotating. The fasteners of the present invention are aimed at eliminating this problem.

Figure 28:
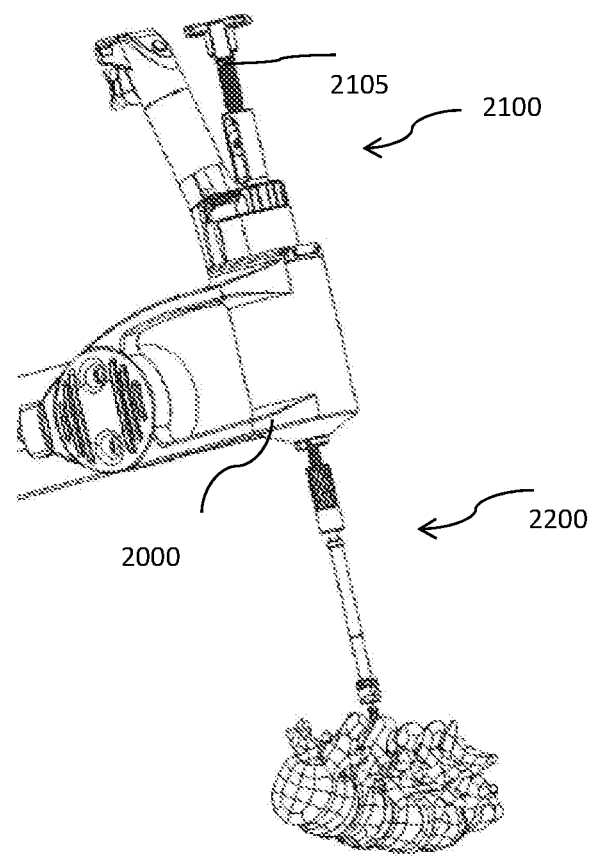
FIG. 28 is a schematic view of an advancement device in conjunction with a robotic end effector in accordance with an aspect of the present disclosure.
Figure 29:
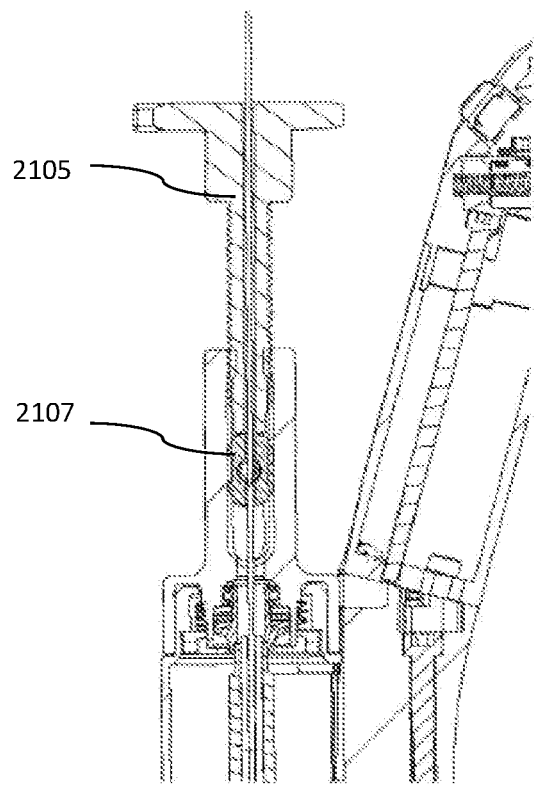
FIG. 29 is a cross-sectional view of the advancement device of FIG. 28.
Figure 30:
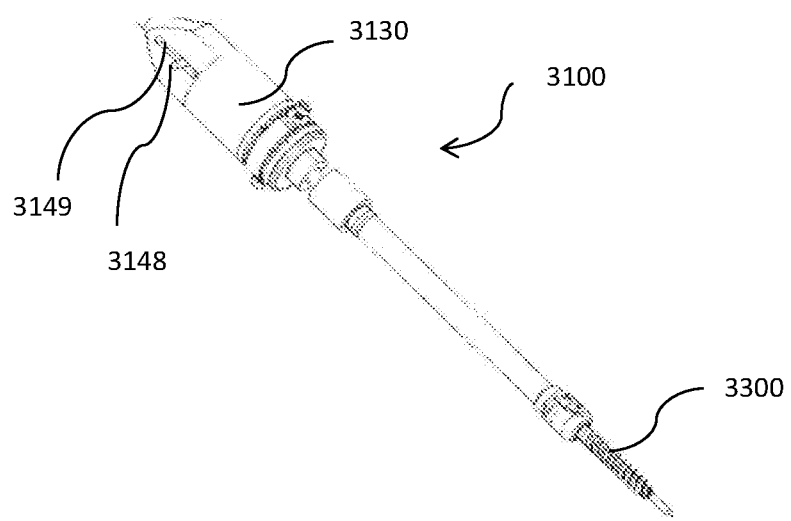
FIG. 30 is a perspective view of a placement device according to another embodiment of the present disclosure.

The step of advancing the stylet into the bone can be performed with the use of a robotic end effector 2000 and an advancement mechanism 2100 positioned at a proximal end of robotic end effector 2000. In the illustrated embodiment, shown in FIGS. 28 and 29, advancement mechanism 2100 includes threaded knob 2105 which engages the stylet as threaded knob 2105 is rotated in a first direction. As threaded knob 2105 is advanced distally, the stylet translates distally through a screwdriver 2200 and through the cannulated channel of the attached fastener. The stylet is connected to a sliding coupler 2107 that travels axially within the advancement mechanism. The coupler is attached to the stylet via a set screw to secure the stylet to the coupler. Once the stylet is advanced to the desired depth, threaded knob 2105 can be disengaged from the stylet and removed such that the stylet remains secured within the bone while the fastener is then rotated to advance the fastener into the bone. In alternative embodiments, advancement mechanism 2100 can include a spring, cam or gear in place of the threading to advance the stylet distally through screwdriver 2000 and the attached fastener.

FIGS. 30-37 show a placement device 3100 that may be used to place a stylet and fastener into the bone. Placement device 3100 may be used with robotic end effector 2000 or may be used during manual insertion. Placement device 3100 allows the stylet to oscillate back and forth between clockwise and counter clockwise directions while the fastener is advanced over the stylet in just one of those rotational directions and threaded into bone.

Figure 31:
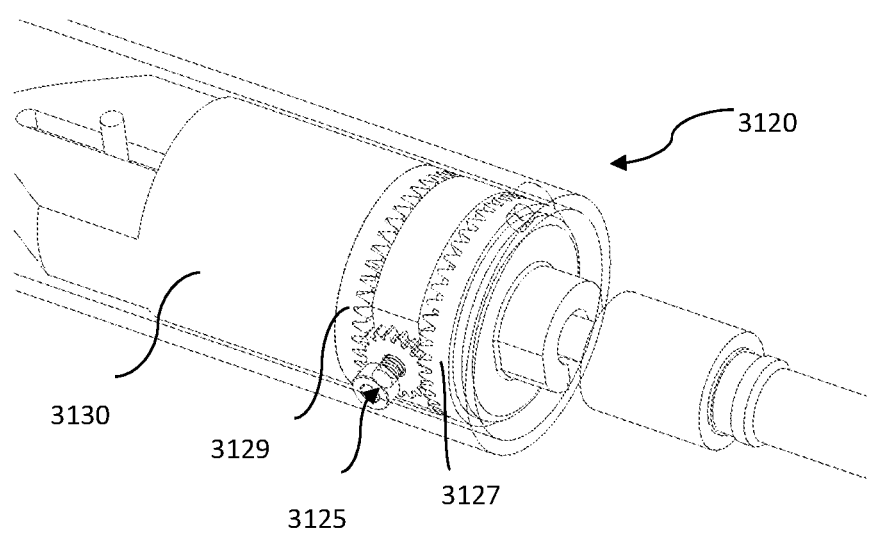
FIG. 31 is an enlarged view of a drive mechanism of the placement device of FIG. 30.
Figure 32:
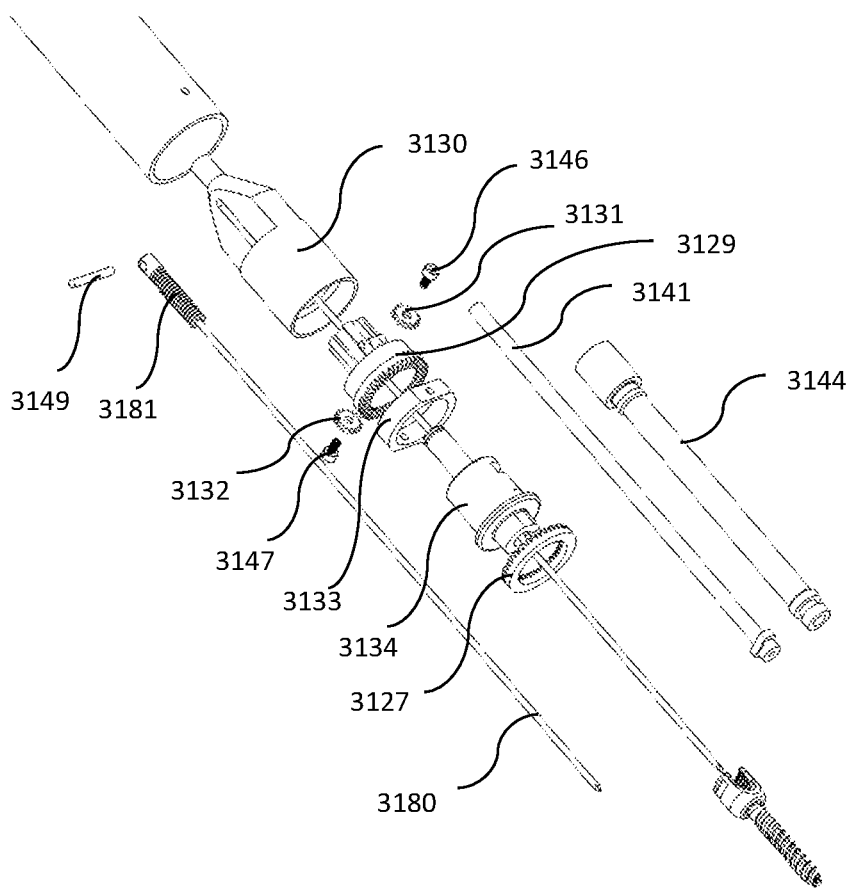
FIG. 32 is an exploded view of the placement device of FIG. 30.
Figure 33:
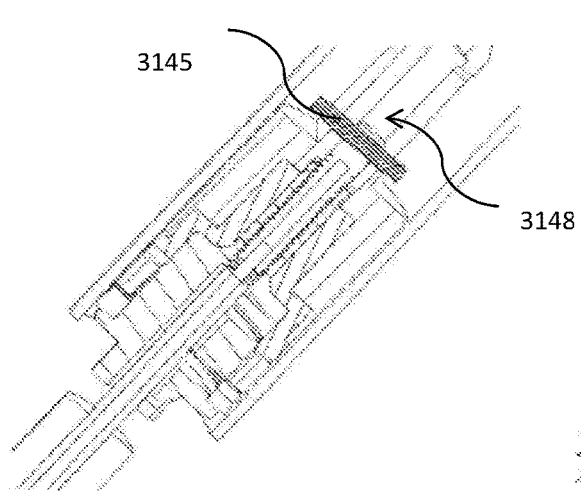
FIGS. 33 and 34 are cross-sectional views of the placement device of FIG. 30.
Figure 34:
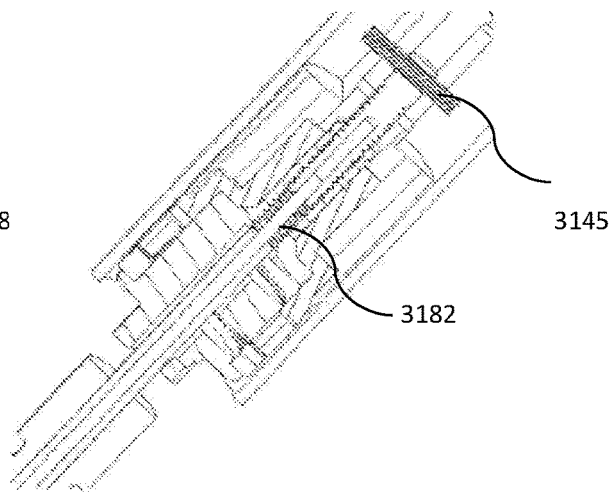
Figure 35:
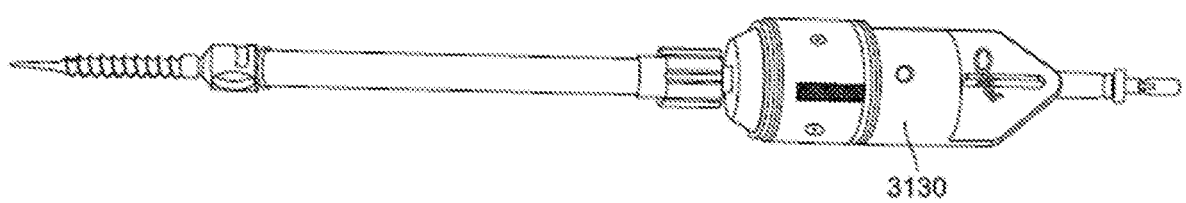
FIG. 35 is a side view of the placement device of FIG. 30.
Figure 37:
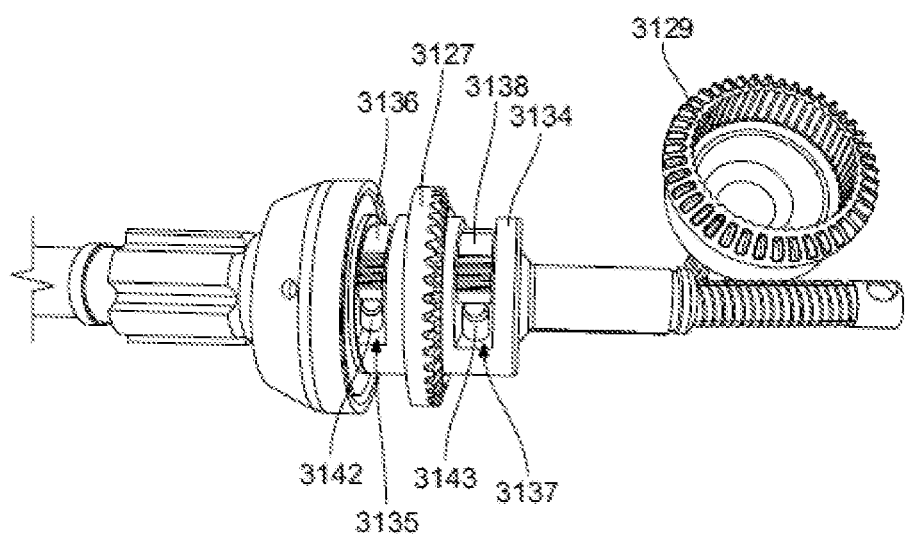
FIG. 37 is a side view of the double drive mechanism of the placement device of FIG. 30.

Placement device 3100 includes a drill adaptor 3130 through which the motor of end effector 2000 can be connected to device 3100. Drill adaptor 3130 communicates with a double drive mechanism 3120, as best shown in FIGS. 31, 32, and 37. Double drive mechanism 3120 includes gear system 3125 formed of a driving gear 3129 and a driven gear 3127. Driving gear 3129 has a splined outer surface at its proximal end that mates with a complimentary splined internal surface (not shown) of the drill adaptor 3130 so that rotation of drill adaptor 3130 is translated into rotation of driving gear 3129. Driving gear 3129 is connected to driven gear 3127 through two connector gears 3131, 3132 disposed at opposite sides of a collar 3133. Through this connection, rotational movement of driving gear 3129 in one direction, e.g. clockwise, corresponds to rotational movement of driven gear 3127 in the opposite direction, e.g. counter clockwise.

Figure 36:
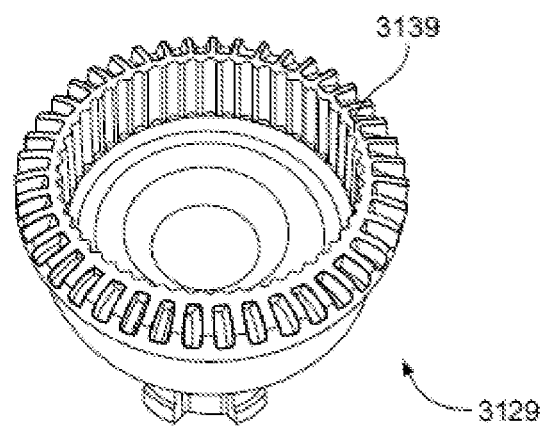
FIG. 36 is a perspective side view of the driving gear of the placement device of FIG. 30.

A housing 3134 is disposed within the circumferences of driving gear 3129, driven gear 3127, and collar 3133. Housing 3134 has two recesses 3135, 3137 in which ratcheted pawls 3136, 3138, respectively, are disposed, as shown in FIG. 37. In FIG. 37, driven gear 3127 is shown in a misaligned state so that pawl 3136 is exposed, and driving gear 3129 is removed to expose pawl 3138. As shown in FIG. 36, an internal circumferential surface 3139 of driving gear 3129 is splined for communication with the ratcheted outer surface of pawl 3138. An internal circumferential surface (not shown) of driven gear 3127 is similarly splined for communication with the ratcheted outer surface of pawl 3136. Both of pawls 3136, 3138 are ratcheted in the same direction about the axis of device 3100. When one gear is in ratcheted connection with its pawl, the other gear slips past its pawl, and vice versa.

Pawl 3136 is connectable to a screw driver shaft 3141 through a pin 3142. Similarly, pawl 3138 is connectable to screw driver shaft 3141 through a pin 3143. Since pawls 3136, 3138 are both ratcheted in the same direction while gears 3127, 3129 disposed circumferentially above them are connected in opposite rotational directions, this dictates that rotational motion of housing 3134 will always only be driven by one of gears 3127, 3129 through its respective pawl 3136, 3138. That is, when driving gear 3129 is rotated in a direction to engage with pawl 3138, pawl 3138 engages screw driver shaft 3141 so that housing 3134 is rotationally locked with screw driver shaft 3141. Also, when driven gear 3127 is rotated in a direction to engage with pawl 3136, pawl 3136 engages screw driver shaft 3141 so that housing 3134 is rotationally locked with screw driver shaft 3141. The opposite rotational directions of gears 3127, 3129 therefore dictate that screw driver shaft 3141 will always be rotationally locked with housing 3134 and that housing 3134 will always be rotated in the same direction regardless of the direction in which drill adaptor 3130 is rotated.

Based on the structural makeup of device 3100 as described above, rotation of drill adaptor 3130 in either direction (i.e. clockwise or counter clockwise) will result in rotation of screw driver shaft 3141 in a single direction (i.e. only clockwise or only counter clockwise). As device 3100 is configured for insertion of a fastener, the direction screw driver shaft 3141 rotates is clockwise by right-hand rule. A distal end of screw driver shaft 3141 is noncircular to mate with the tulip of the fastener to facilitate insertion. A screw driver sleeve 3144 is disposed about screw driver shaft 3141 such that screw driver shaft 3141 can rotate therein. A distal end of screw driver sleeve 3144 has an annular depression in which interior flanges of each prong of the tulip can be seated to maintain the fastener at the end of device 3100, particularly as it is advanced toward the surgical site.

The operation of gear system 3125 is made possible because an outer housing 3145 is held stationary (i.e. non rotatable) during operation of device 3100. Outer housing 3145 is either held by the user or connected to the end effector 2200 during operation. Pins 3146, 3147 are anchored to outer housing 3145, through connector gears 3131, 3132, respectively, and into collar 3133. This allows drill adaptor 3130 to be rotationally connected to driving gear 3129 and driven gear 3127, and ultimately to housing 3134 to drive screw driver shaft 3141, which in turn drives the fastener.

Another simultaneous function of driver 3100 is that it can rotate a stylet 3180 through a threaded proximal end 3181 of stylet 3180. A threaded internal surface 3182 of housing 3134 is threadedly connected with threaded proximal end 3181. Also, a pin 3149 is disposed through housing an aperture in threaded proximal end 3181 and protrudes through a slot in drill adaptor 3130 at either end, so that rotation of drill adaptor 3130 in one direction (i.e. clockwise or counter clockwise) always corresponds with rotation of stylet 3180 in the same direction (i.e. clockwise or counter clockwise, respectively) as drill adaptor 3130. Thus, when drill adaptor 3130 is oscillated, stylet 3180 is also oscillated. When drill adaptor 3130 is rotated in one direction, stylet 3180 is rotated along with it.

The threaded connection of stylet 3180 with housing 3134 adds a further useful dimension to device 3100 since housing 3134 is axially stationary along device 3100 though it rotates in one direction due to double drive mechanism 3125. Assuming device 3100 is configured so that clockwise rotation by right-hand rule advances the fastener distally, during clockwise rotation of drill adaptor 3130, torque is transmitted by the slot in drill adaptor 3130 via pin 3149 to stylet 3180, and stylet 3180 is simply driven in the same clockwise direction, though no translation of stylet 3180 occurs. The threads of threaded proximal end 3181 and housing 3134 are of the same pitch. When stylet 3180 and housing 3134 both rotate in the same direction, there is no relative movement between their threads. When the input motion is reversed to counter clockwise rotation of drill adaptor 3130, stylet 3180 once again follows in the same counter clockwise direction of drill adaptor 3130, but since it is threaded to housing 3134 that is rotating in the opposite clockwise direction, the relative motion between the mating threads causes an axial translation of stylet 3180, having the effect of incremental retraction. The slot in drill housing 3130 through which pin 3149 is disposed accommodates translation of stylet 3180. The position of the pin 3149 along the length of the slot can serve as an indicator for where the tip of stylet 3180 is relative to the tip of the fastener, and could include depth markings to give a more precise indication. Selecting a particular pitch and lead of threads dictates how much axial translation occurs for a given angular rotation of drill housing 3130. Additionally selecting a particular pitch and lead of thread on the fastener dictates how much relative axial translation occurs between the bone and stylet 3180.

Any of the previously described rotations or translations could be reversed to achieve alternative surgical goals, such as progressively advancing stylet 3180 or maintaining a constant stylet 3180 depth relative to the bone. A simple switch can also be provided to allow the user to mechanically select between "forward" (as described above) and "reverse" modes of device 3100.

Spine surgeons currently use a natural oscillating motion to advance instruments into the spine to create a pilot hole in the pedicle to prepare for screw insertion. For example, a surgeon will twist an awl, gearshift, or jamshidi needle back and forth to carefully advance it to the desired depth. While device 3100 can be utilized either electronically (via power or a robot) or manually by hand, it captures this desired oscillating motion while simultaneously driving the fastener over the stylet in a single, efficient tool.

Figure 38:
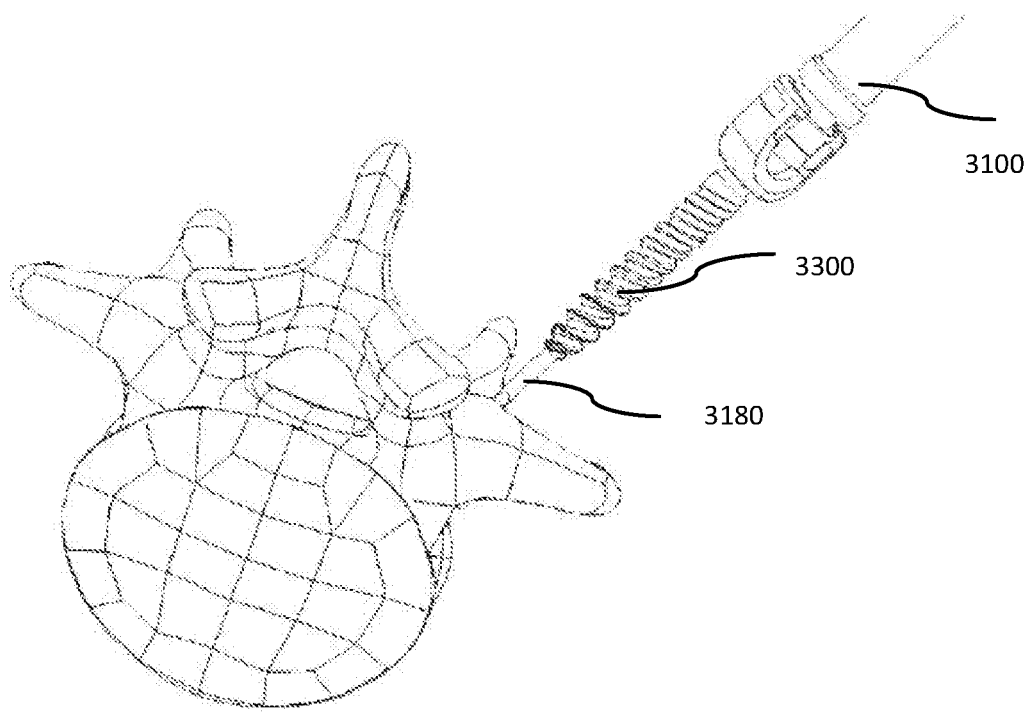
FIGS. 38-41 are schematic representations of the placement device of FIG. 30 in conjunction with a stylet and a screw.
Figure 39:
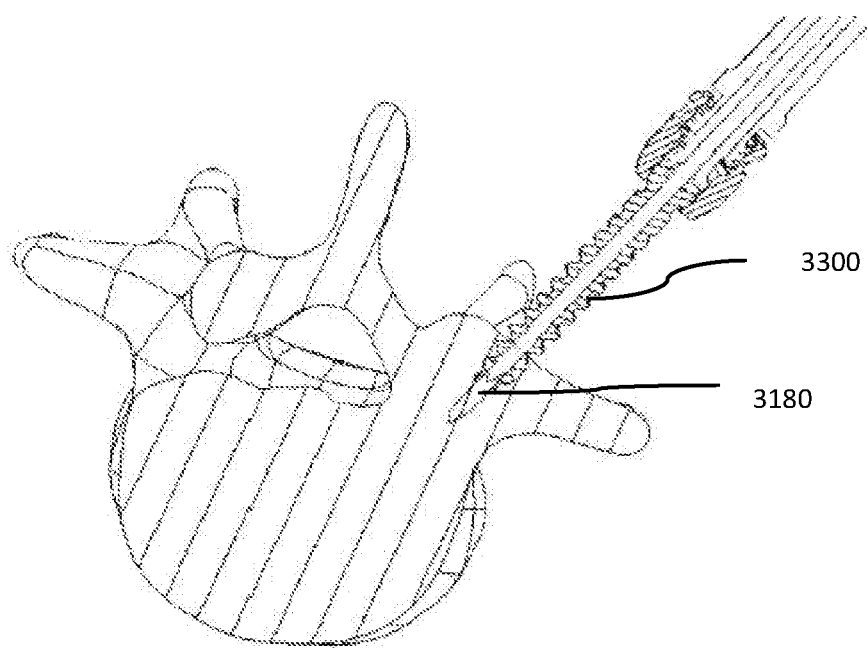
Figure 40:
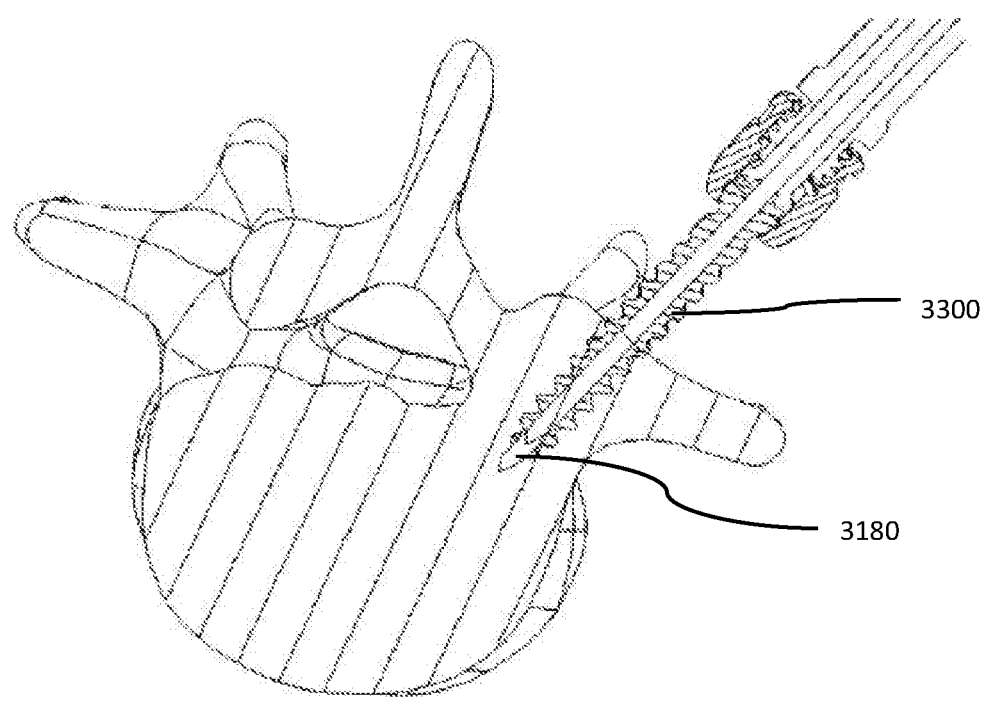
Figure 41:
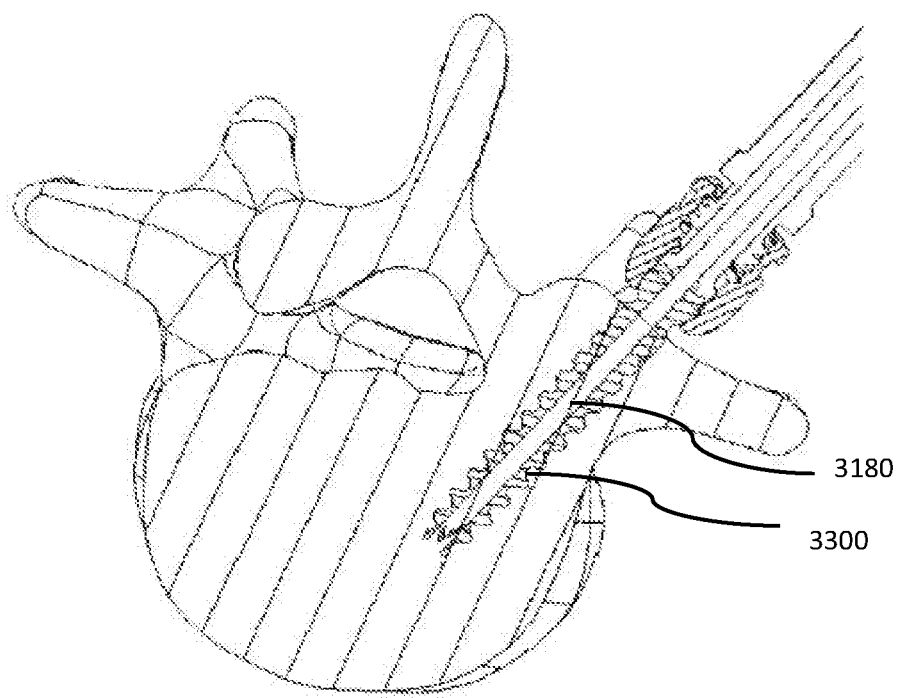

During use of device 3100, stylet 3180 is first loaded by setting it to the proper depth relative to the length of the intended fastener. Since device 3100 is configured to either maintain the axial position of stylet 3180 or retract it, this is the furthest distally that the tip of stylet 3180 will be positioned relative to the handle of device 3100 during the procedure. A fastener 3300 is then loaded onto device 3100 by placing it over stylet 3100 and connecting it to screw driver shaft 3141. Device 3100 is advanced until the distal tip of stylet 3100 is docked to the bone, as shown in FIG. 38. At this point or during docking, the surgeon can begin to oscillate drill housing 3130 by hand or robotically by keeping outer housing 3145 stationary and not rotating it. This oscillating motion of stylet 3180 during docking prevents tugging on the local tissue and tendons so that the procedure can be carried out most efficiently and with the least disruption to the surrounding anatomy. While this practice is currently used by surgeons, the oscillation of stylet 3180 even when device 3100 is used robotically provides surgeons with comfort that the same technique is being applied during the procedure.

Continued oscillation of drill housing 3130 while device 3100 is being pushed distally embeds the tip of stylet 3180 into the bone until fastener 3300 meets the bone surface. At this point, further oscillation of drill housing 3130 engages the threads of fastener 3300 into the bone to advance fastener 3300, all while fastener is guided by the path set by stylet 3180. Upon each small counter clockwise rotation of drill housing 3130, stylet 3180 retracts along the length of fastener 3300 so that stylet 3180 is retracted simultaneously. In this way, the surgeon can cannulate the pedicle via oscillating rotational motion of a sharp cutting tool such as a stylet or stylet 3180, while simultaneously advancing a cannulated screw or fastener 3300 over stylet 3180, all driven by a single oscillating input motion to device 3100.

In other embodiments similar to device 3100, the threaded connection and automatic retraction of stylet 3180 can be omitted and stylet 3180 can simply be pulled from the surgical site once fastener 3300 is implanted to the appropriate depth.

According to another embodiment of the present disclosure, FIGS. 42-47 show a stylet control system 4000 for selective and controlled axial movement (i.e. advancement and/or retraction) of a stylet for use during surgery in which a cannulated bone screw is inserted into bone around the stylet. Stylet control system 4000 includes control device 4120 for use in conjunction with a threaded stylet 4150 and a screwdriver 4170 during a spinal surgery in which a pedicle screw 4010 is implanted in bone. Control device 4120 may be controlled manually or with a robotic device, such as a robotic end effector.

Bone screw 4010 includes a head portion, a threaded shaft 4011, and a tulip 4020 for coupling the screw to an orthopedic rod. Bone screw 4010 may be a standard size pedicle screw or it may be a screw adapted for use in minimally invasive surgery. Any of the above-described screws are suitable for use in stylet control system 4000. Bone screw 4010 is cannulated such that stylet 4150 can extend through the cannulation and can extend beyond a distal tip of the screw. Bone screw 4010 has a threaded shaft 4011 and its head is received within tulip 4020. Tulip 4020 is designed to receive a stabilizing rod therethrough. An inner surface of tulip 4020 includes threads capable of engaging with the screwdriver 4170, described in further detail below. Further, bone screw 4010 includes a self-cutting feature at its distal end, such as sharp cutting edges.

Figure 43:
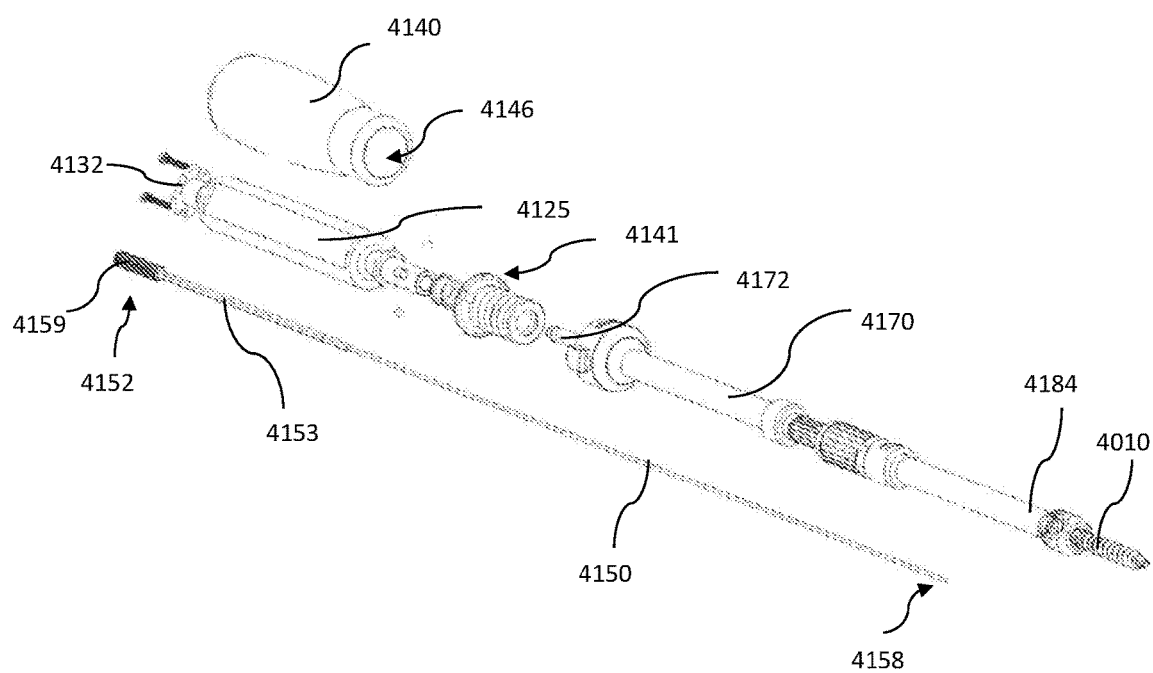
FIG. 43 is an exploded view of the stylet control system of FIG. 42.

Stylet 4150 extends between proximal end 4152 and distal end 4158, which terminates at a sharp distal point to allow the stylet to cut through bone to form a cannulation for ease of insertion of bone screw 4010, as described above. At proximal end 4152, stylet 4150 includes monolithic threaded portion 4159 that facilitates axial translation of the stylet relative to screwdriver 4170 and control device 4120. Stylet 4150 also includes an anti-rotation feature to prevent relative rotation between stylet 4150 and screwdriver 4170. For example, in the illustrated embodiment, stylet 4150 includes keyed hex portion 4153 that has a hexagonal cross section extending along a portion of its length which corresponds to a hex feature on screwdriver 4170, described below. As shown in FIG. 43, hex portion extends from a distal end of threaded portion 4159. Although described herein as a hex, the mechanically keyed feature may be square, oval, triangular, trapezoidal etc.

Figure 44:
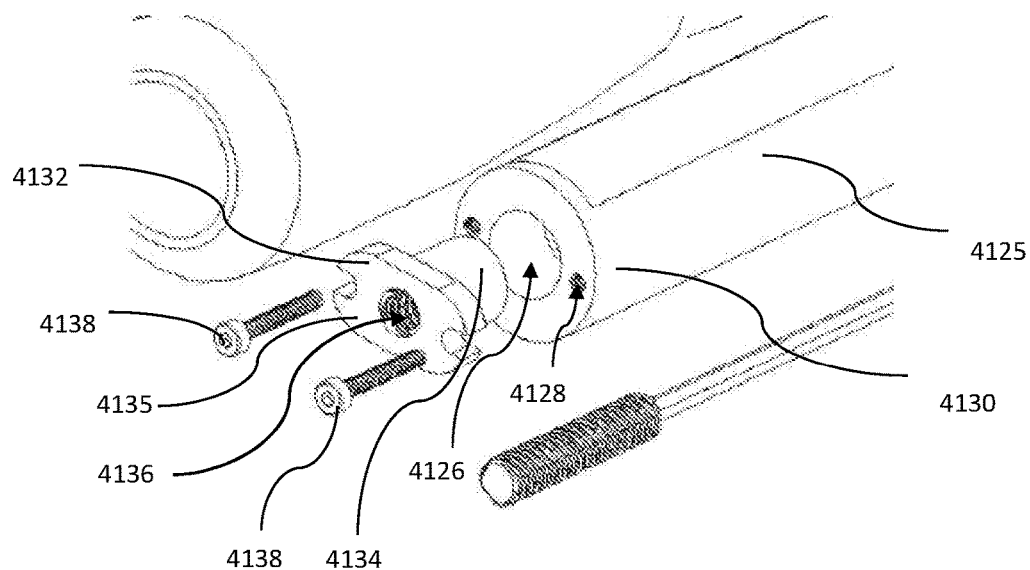
FIG. 44 is an enlarged view of the exploded view of the proximal end of the stylet control system of FIG. 43.

Control device 4120 includes proximal assembly 4121 that is rotatable relative to screwdriver 4170. Proximal assembly 4121 includes inner core 4125, coupling member 4132, and outer handle 4140. Inner core 4125 defines central lumen 4126 extending therethrough for receiving stylet 4150. As shown in FIG. 44, control device 4120 includes coupling member 4132 with base 4134 having a generally cylindrical shape and top portion 4135 having a planar surface and a sidewall with opposing cut-outs 4135 for receiving screws 4138, which secure base 4134 to inner core 4125. Base 4134 is sized to fit within central lumen 4126 of inner core 4125. Coupling member 4132 includes a threaded opening 4136 extending through base 4134 and top portion 4135 for engaging threaded portion 4159 of stylet 4150.

Inner core 4125 includes an attachment feature to attach coupling member 4132 to proximal end 4130 of inner core 4125. In the illustrated embodiment, the attachment feature is in the form of two threaded bores 4128 extending into proximal end 4130 of inner core 4125 that are sized for receiving set screws 4138. With coupling member 4132 axially and rotationally secured to inner core 4125, threaded opening 4136 of the coupling member is coaxial with central lumen 4126 of the inner core so that stylet 4150 can extend through the assembly. In other examples, coupling member 4132 may be integral or monolithic with inner core 4125.

Control device 4120 also includes outer handle 4140 housing coupling member 4132 and inner core 4125. Outer handle 4140 defines central lumen 4146 extending longitudinally through its entirety. Central lumen 4146 is sized to accommodate inner core 4125. Outer handle 4140 has a rounded outer surface to allow for a user to comfortably grip the handle. Outer handle 4140 is axially and rotatably fixed to inner core 4125 and coupling member 4132 such that when the outer handle 4140 is rotated in a first direction, e g manually or robotically, inner core 4125 and coupling member 4132 are also rotated in the first direction. In the illustrated embodiment shown in FIG. 46, a proximal end of coupling member 4132 extends farther proximally than the proximal end of outer handle 4140, such that threaded opening 4136 is positioned proximal to outer handle 4140. Further, when stylet 4150 is positioned within inner core 4125, a portion of stylet 4150 extends proximally to outer handle 4140 as shown in FIG. 42.

Figure 45:
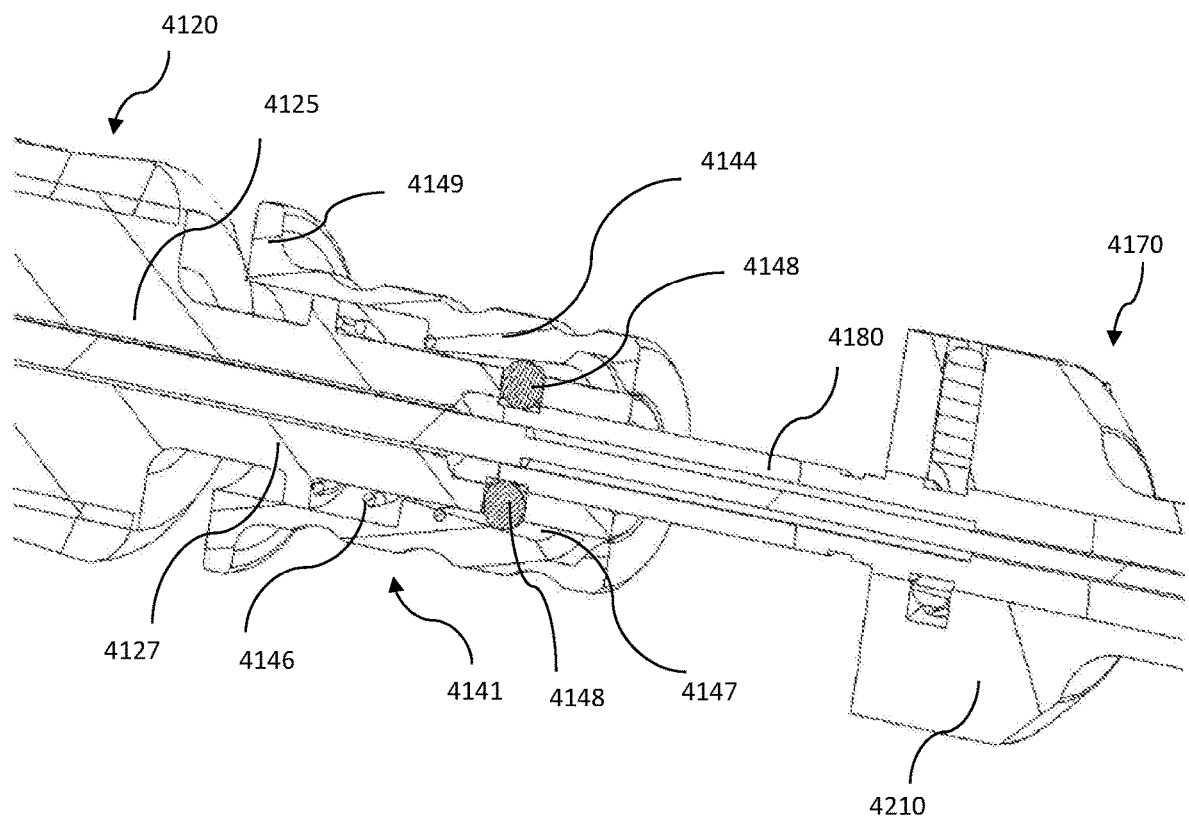
FIG. 45 is a cross-sectional view of a quick connect feature of the stylet control system of FIG. 42.
Figure 46:
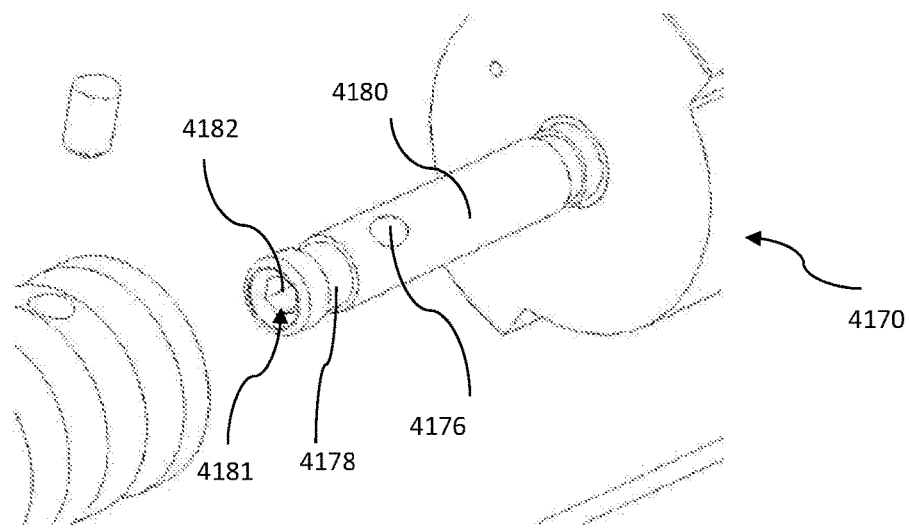
FIG. 46 is a perspective side view of the proximal end of the screwdriver of the stylet control system of FIG. 42.
Figure 47:
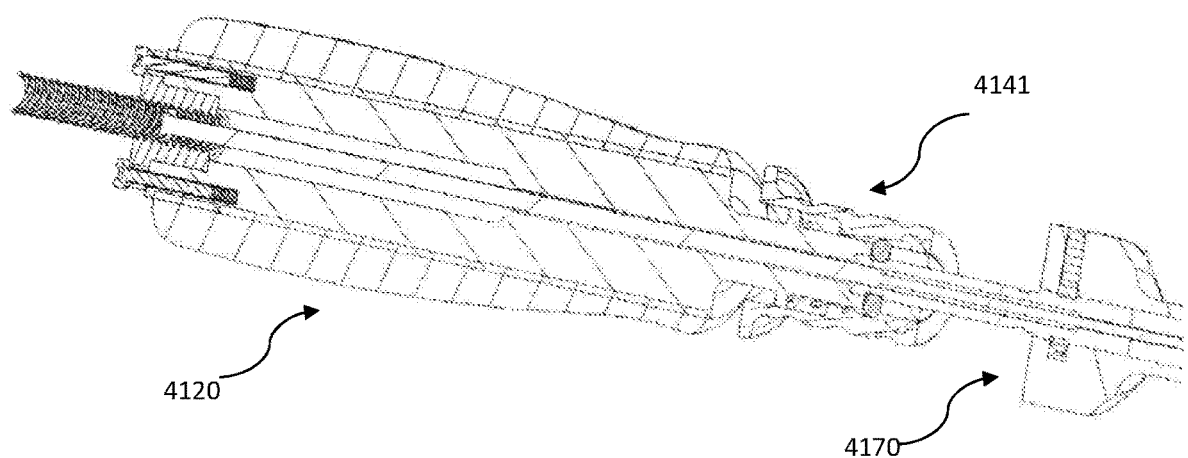
FIG. 47 is a cross-sectional view of the control device of the stylet control system of FIG. 42.

Control device 4120 includes quick connect system 4141 that facilitates a simple and efficient connection to the proximal end of screwdriver 4170, as shown in detail in FIGS. 45-47. Quick connect system 4141 includes a collar 4144 that surrounds a distal shaft 4127 of inner core 4125. An inner shaft 4180 of screwdriver 4170 is connected to collar 4144 via at least one a spring-loaded ball bearing 4148 received within a radial groove 4178 on inner shaft 4180 of screwdriver 4170. When collar 4144 is located radially outside of radial groove 4178 with the ball bearing disposed within the groove 4178, collar 4144 does not permit the ball bearing 4148 to leave groove 4178, thereby connecting control device 4120 and screwdriver 4170. The engagement of ball bearing 4148 and groove 4178 prevents axially movement of control device 4120 relative to screwdriver 4170 but allows rotation of the control device 4120 relative to the screwdriver 4170. When collar 4144 is moved away, the ball bearing can move radially outward so that control device 4120 and screwdriver 4170 can be disconnected. Screwdriver 4170 also includes recess 4176 for attaching an alternative quick connect in the event the user wants to use a standard handle to manually drive the screw into bone.

The quick connect system 4141 may be released by applying an axial force in the proximal direction, which may be applied by a user to collar flange 4149, to remove the radial load applied against the screwdriver 4170 to disengage the screwdriver from the control device 4120.

Figure 42:
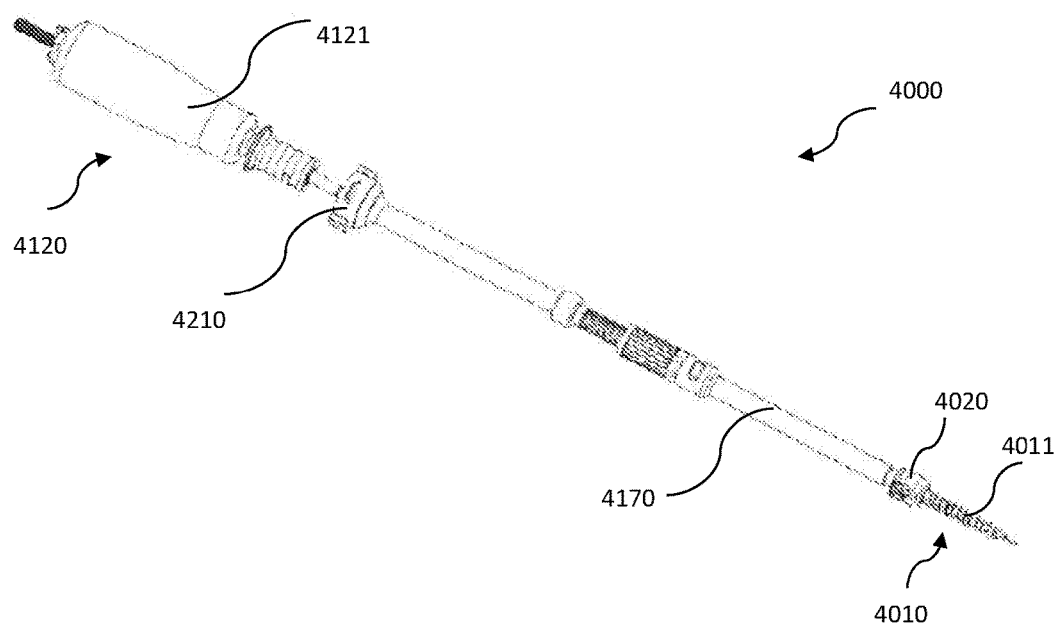
FIG. 42 is a perspective side view of a stylet control system according to an embodiment of the present disclosure.

Referring to FIGS. 42 and 43, screwdriver 4170 extends between proximal end 4172 and distal end 4184. Distal end 4184 is configured for securing to and engaging a screw, such as pedicle screw 4010. Screwdriver 4170 may be used with mono-axial pedicle screws, poly-axial pedicle screws, reduction screws, or screws designed for minimally invasive surgeries (MIS screws).

At distal end 4184, screwdriver 4170 engages screw 4010. An outer sleeve may include external threaded portion configured to thread into corresponding threads on the inner surface of the tulip 4020 of screw 4010. Inner shaft 4180 is positioned concentrically within the outer sleeve and includes a driving member for engagement within a corresponding opening of the head of bone screw 4010. The driving member may be hexagonally shaped designed to torque bone screw 4010 to advance the screw into bone. Alternatively, inner shaft 4180 may include threads to engage the threads of tulip 4020 of screw 4010.

Inner shaft 4180 is cannulated along its length and defines inner lumen 4181 to allow stylet 4150 to extend entirely through the shaft and through bone screw 4010. Inner shaft 4180 includes an anti-rotation feature at its proximal end to prevent stylet 4150 from rotating relative to screwdriver 4170. In this manner, stylet 4150 is rotationally coupled with screwdriver 4170, and both are rotatable relative to proximal handle assembly 4121. In the illustrated embodiment, the anti-rotation feature includes a hex-shaped inner surface 4182 surrounding inner lumen 4181 on at least the proximal end of the screwdriver 4170. Hex portion 4153 on stylet 4150 is sized and shaped to fit within inner shaft 4180 without relative rotational movement between the hex members 4153, 4182, thus rotationally coupling the elements.

Figure 48:
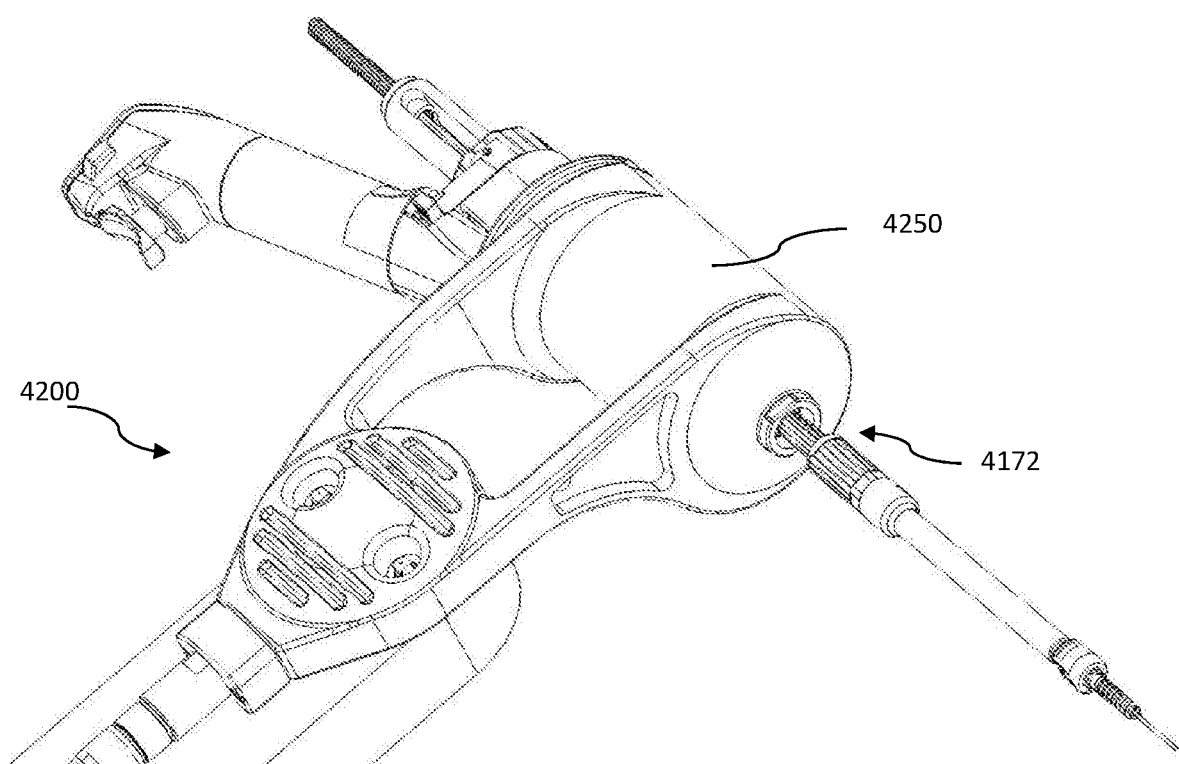
FIG. 48 is a perspective side view of a robotically operative stylet control system in conjunction with a robotic device according to an aspect of the present disclosure.

System 4000 is also designed for use in robot-assisted surgery and can be connected to a robotic device to facilitate the torqueing of bone screw 4010 into the bone and/or to facilitate the movement of stylet 4150. In other examples, system 4000 can be manually operated in part, i.e. control device 4120 may be manually operated while the screwdriver is robotically operated, or both pieces can be either robotically or manually operated. For example, as shown in FIG. 48, a robotic device 4200 including a robotic arm with a rotatable end effector coupled to the end of the robotic arm can interface with a robotic unit coupler positioned on proximal end 4172 of screwdriver 4170. The robotic coupler includes at least one tab for transmitting torque to the screwdriver. End effector 4210 transmits torque to inner shaft 4180 to rotate the shaft 4180 in a clockwise direction to advance the screw in bone. When the control device 4120 is held stationary during this robotic rotation of screwdriver 4170, stylet 4150 retracts proximally.

To assemble system 4000, stylet 4150 is first advanced through control device 4120 and threaded portion 4159 of stylet 4150 is threaded into threaded opening 4136 of coupling member 4132. Control device 4120 is then loaded onto screwdriver 4170 via quick connect system 4141, while stylet 4150 is positioned through the assembled device such that it extends through the distal end of bone screw 4010. When the stylet 4150 is loaded into the screwdriver 4170, stylet 4150 is rotationally fixed relative to the screwdriver due to the mating hex features 4182, 4153 of the screwdriver and the stylet.

In operation, with distal end 4158 of stylet 4150 positioned against bone, proximal handle assembly 4121 is rotated by rotating outer handle 4140 in a first direction, such as in the clockwise direction. When outer handle 4140 is rotated in the first direction, screwdriver 4170 is held stationary and is not rotated, which produces relative rotational movement between control device 4120 and screwdriver 4170. The rotation of outer handle 4140 causes inner core 4125 to rotate so that threads of threaded opening 4136 of inner core engage threads of threaded portion 4159 of stylet 4150. Screwdriver 4170 is held stationary, meaning that stylet 4150 is also not rotated. Thus, as threaded portions 4136, 4159 engage each other, stylet 4150 advances axially through control device 4120 and screwdriver 4170, i.e. stylet 4150 travels in the distal direction, based on the threaded engagement. As stylet 4150 moves distally it travels through bone and produces a path having the desired trajectory for the bone screw to follow, while the shaft of the bone screw 4010 remains placed on or above the bone. Once stylet 4150 is advanced to the desired depth in the bone, which may be about 5 to 30 millimeters, bone screw 4010 can be implanted over stylet 4150 to maintain the desired trajectory of the bone screw. Because bone screw 4010 advances over stylet 4150, this helps to prevent skiving of the tip of bone screw 4010 relative to the intended entry point in the bone. In the example of robotic operation of the screwdriver 4170, the end effector 4210 keeps the screwdriver stationary to insert stylet 4150 without impaction.

It is advantageous to advance bone screw 4010 into bone without further advancing stylet 4150 beyond the desired depth. In order to do so, proximal handle assembly 4121 is held stationary while screwdriver 4170 is rotated in a clockwise direction. When screwdriver 4170 is rotated clockwise, manually or robotically, inner shaft 4180 of the screwdriver 4170 rotates in this direction which drives bone screw 4010 into bone. As screwdriver 4170 is rotated, and thus stylet 4150 rotates while proximal handle assembly 4121 remains stationary, stylet 4150 travels axially in the retraction direction, i.e. proximally. It may be advantageous that the pitch of the threads of the stylet are the same as the pitch of the threads of the bone screw, which results in the stylet retracting at the same rate as the bone screw is advanced.

In another embodiment according to the present disclosure, control device 4120 is built into the robotic end effector 4250. A back coupler is attached to end effector 4250 which functions as control device 4120 and facilitates the relative rotational movement of the screwdriver 4170 and the back coupler to control the movement of stylet 4150 in the proximal and distal directions, as desired. When screwdriver 4170 is driven in the counter-clockwise direction by the end effector 4250, stylet 4150 rotates with screwdriver 4170 causing the stylet 4150 to rotate relative to the back coupler. This relative rotation causes stylet 4150 to advance axially in the distal direction to advance into bone. When the end effector 4250 rotates screwdriver 4170 clockwise, stylet 4150 translates axially in the proximal direction as screwdriver 4170 simultaneously drives the fastener into bone.

Figure 49:
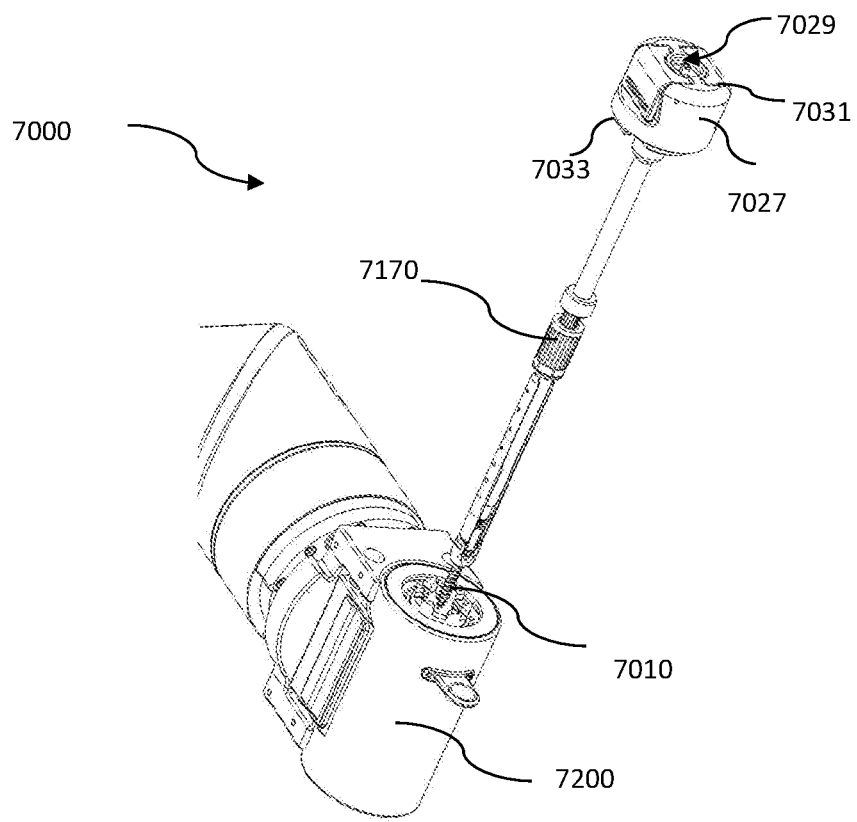
FIGS. 49-53 are perspective side views of a robotically operative stylet control system in conjunction with a robotic device according to an aspect of the present disclosure.
Figure 50:
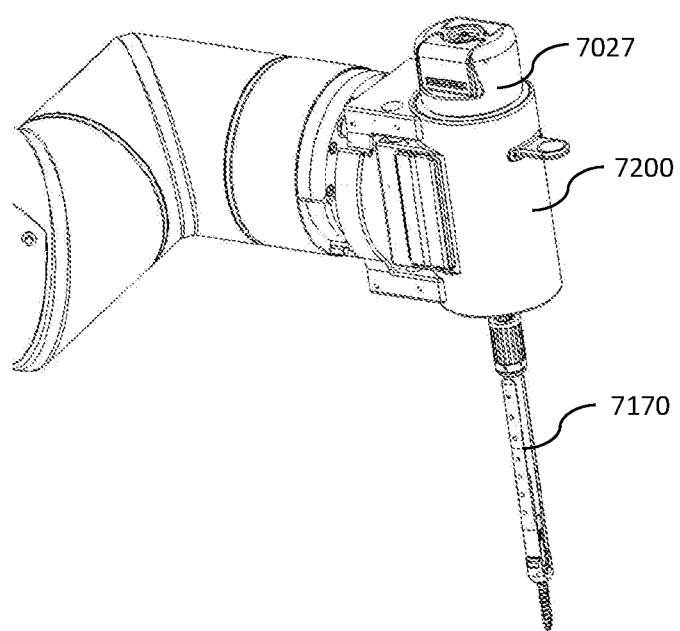
Figure 51:
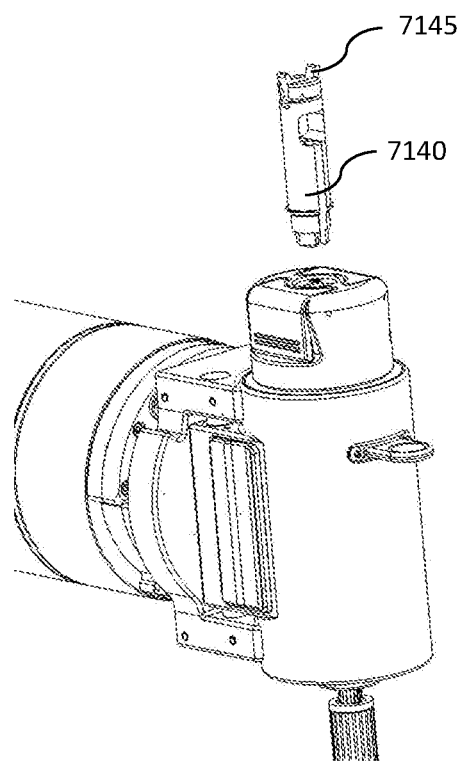

FIGS. 49-54 show stylet control system 7000, which is built into end effector 7200. Control system 7000 includes cap 7027 which forms a connection between the end effector and the instrument for use, e.g. screwdriver 7170. Cap 7027 defines passage 7029 which extends from proximal end 7031 to distal end 7033 of cap 7027 and is sized and shaped to receive screwdriver 7170 into at least a distal portion of passage 7029. Cap 7027 is configured to be attached to a proximal end of control system 7000, as shown in FIG. 50.

Screwdriver 7170, with bone screw 7010 attached to a distal end thereof, is positioned within passage 7029 and attached to cap 7027. As shown in FIGS. 49 and 50, screwdriver 7170 extends distally from cap 7027. Cap 7027 is then attached to end effector 7200 such that screwdriver 7170 is in operative engagement with the end effector. Cap 7027 may be designed as a universal cap which configured to attach to various instruments for use during preparation of the bone and implantation of an implant therein, e.g. screwdriver, drill, burr etc.

Control system 7000 further includes stylet 7150 which includes threaded portion 7159 at a proximal end thereof. At least a portion 7153 of the length of stylet 7150 is keyed and screwdriver 7140 includes an anti-rotation feature, such as a corresponding keyed feature to prevent relative rotation between stylet 7150 and screwdriver 7140 while allowing axial movement of the stylet within the screwdriver. In the illustrated embodiment, the keyed feature is shown as a hex, although the mechanically keyed feature may be square, oval, triangular, trapezoidal etc. Control system 7000 includes stylet feeder 7140 sized such that at least a portion of the stylet feeder 7140 is received within a proximal portion of passage 7029 of cap 7027. A portion of stylet feeder 7140 is keyed to prevent relative rotation of the stylet feeder within cap 7027. Stylet feeder 7140 includes hinged threaded pawl 7145, the threads of which are configured to facilitate one-way engagement of threaded portion 7159 of stylet 7150, e.g. engagement to cause proximal movement of the stylet during the rotation of the stylet, while disengaging for distal advancement of the stylet. In this regard, rotation of screwdriver during advancement of bone screw 7010 into bone causes rotation of stylet 7150 and thus engagement of threaded pawl 7145 with threaded portion 7159 of stylet 7150. This engagement results in proximal movement, e.g. retraction, of stylet 7150 as the bone screw is advanced into bone. It may be advantageous that the pitch of the threads of the stylet are the same as the pitch of the threads of the bone screw, which results in the stylet retracting at the same rate as the bone screw is advanced. Of course, this is not required in all embodiments and there may be some benefit to having the stylet designed to retract at a different rate.

Figure 52:
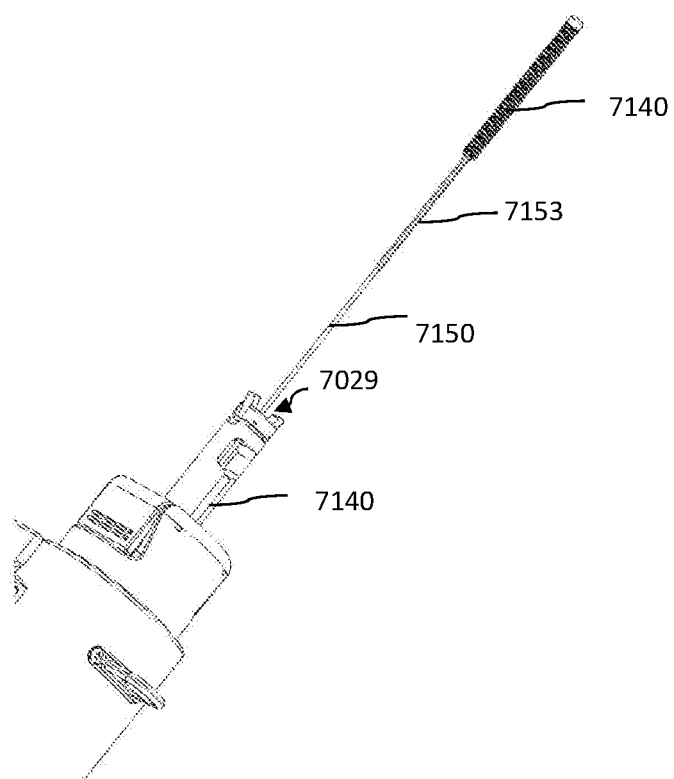
Figure 53:
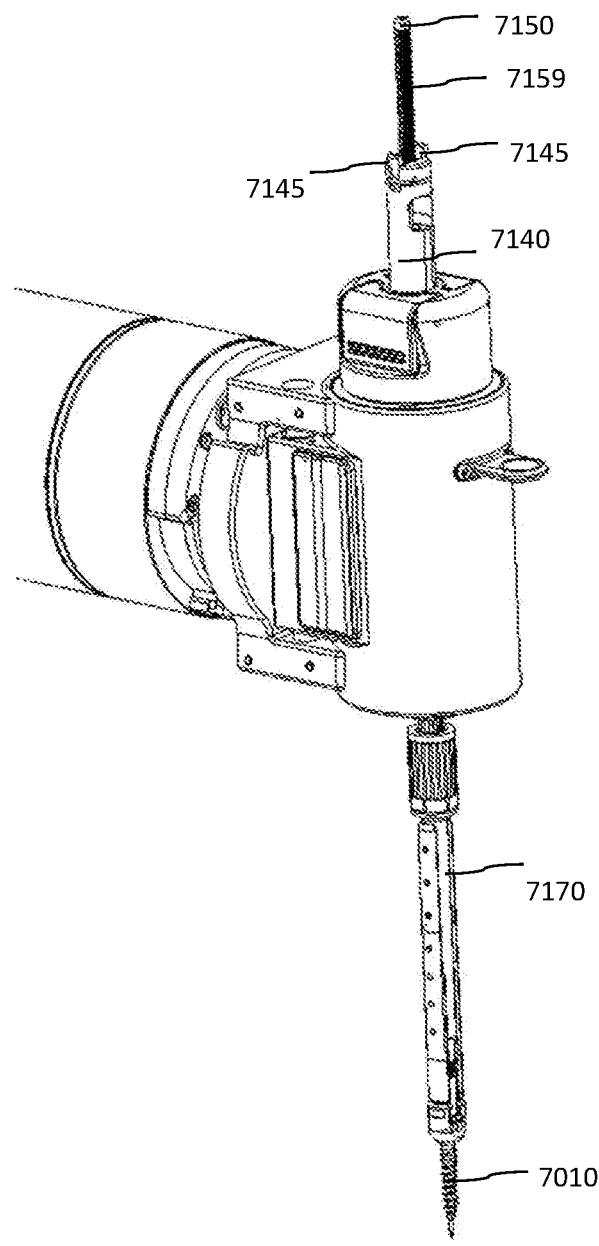
Figure 54:
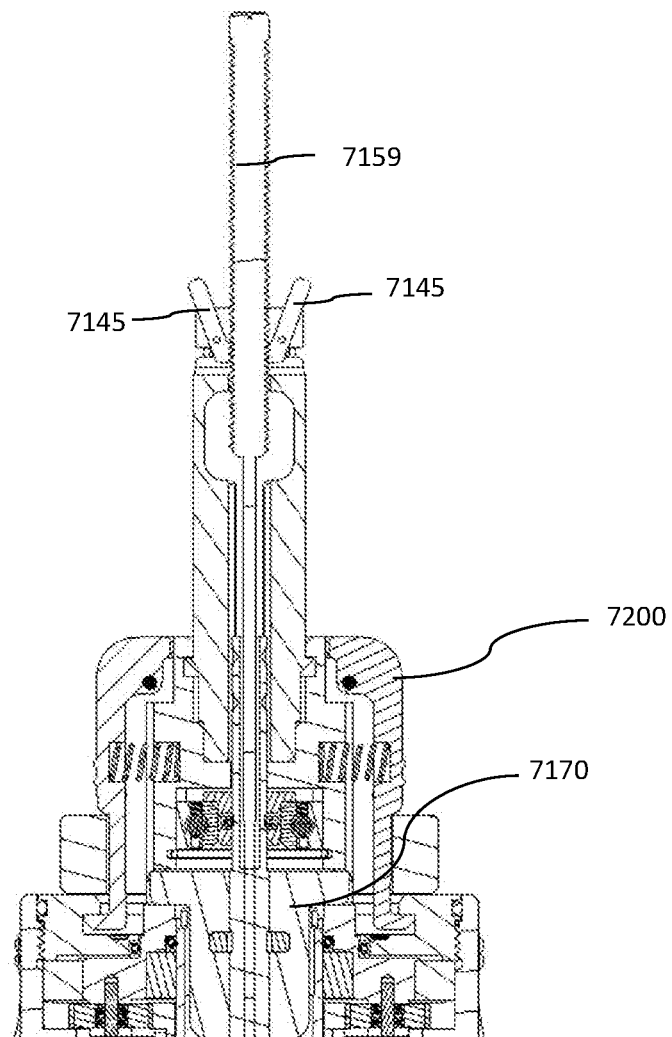
FIG. 54 is a cross-sectional view of the control system of FIGS. 49-53.

As shown in FIG. 52, during use, stylet 7150 is inserted into stylet feeder 7140 such that the stylet extends through screwdriver 7140 and bone screw 7010 so that the distal tip of stylet 7150 extends just beyond the distal tip of bone screw 7010. Stylet 7150 can then be impacted to dock the screw to the bone, such impaction can be done manually such as by hammering or ultrasonically, such ultrasonic advancement of the stylet is described below with reference to FIGS. 55-58. Stylet 7150 may be impacted into the bone to a depth of between about 10 mm to 20 mm Once stylet 7150 is advanced to the desired depth, screwdriver 7170 is driven to advance bone screw 7010 into bone, which causes simultaneous retraction of stylet 7150. After stylet 7150 is advanced to the desired depth in the bone, screwdriver 7170 is driven via end effector 7200 which rotates both the screwdriver and stylet 7150, since the stylet is keyed to the screwdriver. As bone screw 7010 is driven into bone along the trajectory defined by previously implanted stylet 7150, the threaded portion 7159 of stylet 7150 is engaged by pawls 7145, which causes proximal movement, e.g. retraction, of stylet 7150 as the bone screw is advanced into bone.

According to another embodiment of the present disclosure, FIGS. 55-58 show a robotic stylet control device 5000.

Control device 5000 shares many similar to features as control device 4000 and control system 7000, described above in connection with FIGS. 42-47 and FIGS. 48-53, respectively, although control device 5000 is designed to facilitate ultrasonic movement and oscillation of a stylet as it is advanced into bone. Control device 5000 allows for movement of a stylet through a cannulated bone fastener, such as bone fasteners 100-500 and 1300-1900 or a cannulated drill, shown in FIG. 58. Control device 5000 provides controlled axial movement (advancement and/or retraction) of a stylet during surgery including implantation of a cannulated bone fastener. The stylet is advanced into bone to create the initial pilot hole for subsequent insertion of the screw. Additionally, the control device 5000 ultrasonically oscillates during axial movement of the stylet. Such oscillation reduces the applied forces at the bone interface during the advancement of the stylet, which improves robotic accuracy as it minimizes the potential of deflection of the robotic arm. The reduction of force and increased accuracy may also result in a decreased likelihood of skiving.

Traditionally, in during manual preparation of a site for implantation of a bone screw, the process includes multiple steps including: awling, probing, tapping and then placement of the screw. Whereas, with the use of control device 5000, the initial pilot hole is created with the stylet which is received within either a cannulated drill or a cannulated bone screw. Thus, control device 5000 is advantageously procedurally efficient as it eliminates the need for the traditional steps of pilot hole creation.

Figure 55:
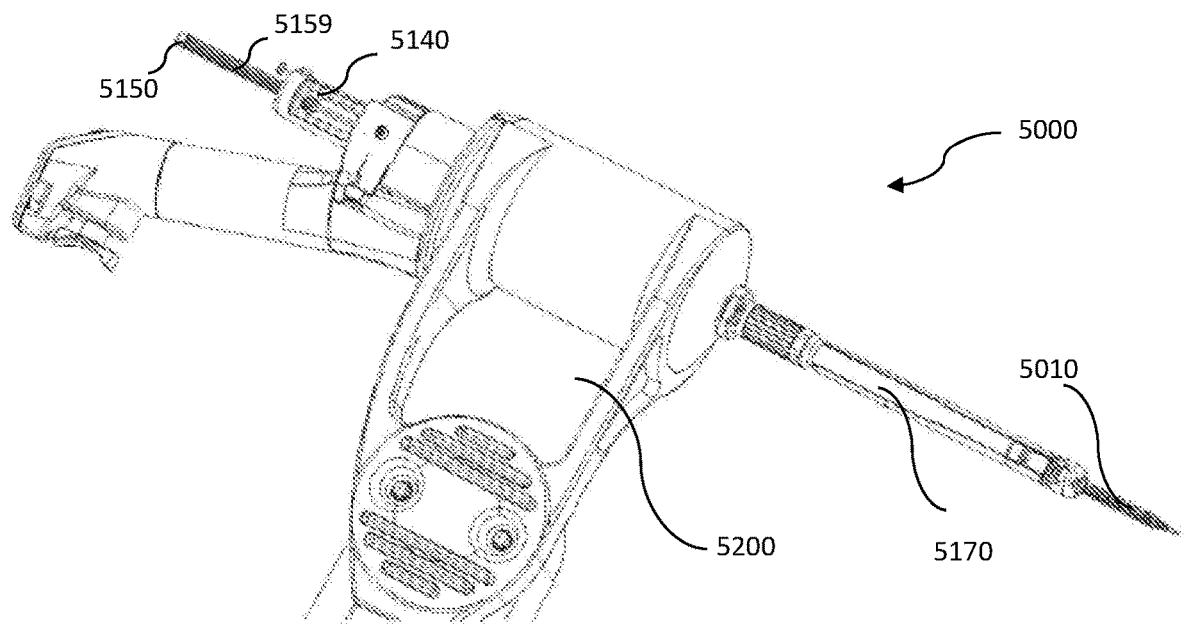
FIG. 55 is a perspective side view of an ultrasonic stylet control device in conjunction with a robotic device according to an aspect of the present disclosure.
Figure 56:
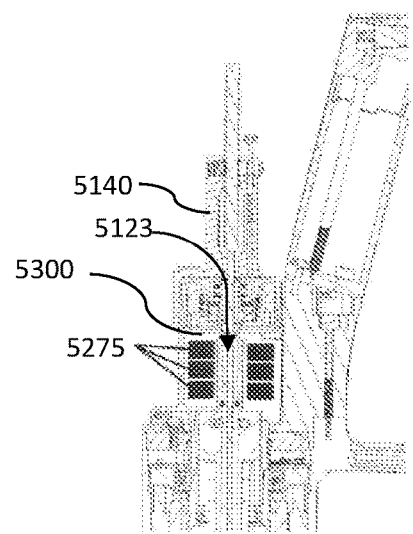
FIG. 56 is a cross-sectional view of the control device of FIG. 55.

Turning to FIGS. 55 and 56, control device 5000 includes housing 5300, retraction assembly 5140, and end effector 5200. Control device 5000 further includes integrated ultrasonic transducers 5275. Housing 5300 defines passage 5310 for receiving stylet 5150. Housing 5300 includes a low gain transducer assembly 5275 for imparting ultrasonic vibrations to stylet 5150. Control device 5000 further includes an energy source for generating the ultrasonic energy.

Transducer assembly 5275 comprises a plurality of piezoelectric elements positioned within housing 5300. Ultrasonic vibration is induced in the end effector by electrically exciting transducers 5275. In this example, transducers 5275 are comprised of piezoelectric elements which produce ultrasonic vibrations. Transducer assembly 5275 are low gain transducers and output frequencies in the range of about 10,000 Hz to about 30,000 Hz. Such ultrasonic vibrations are transmitted to the stylet 5100 positioned within passage 5306 of body 5300.

FIGS. 55 and 56 show control device 5000 in conjunction with screwdriver 5170 and bone screw 5010 attached to the screwdriver. Stylet 5150 includes threaded portion 5159 at its proximal end to facilitate the axial movement of the stylet.

Figure 57:
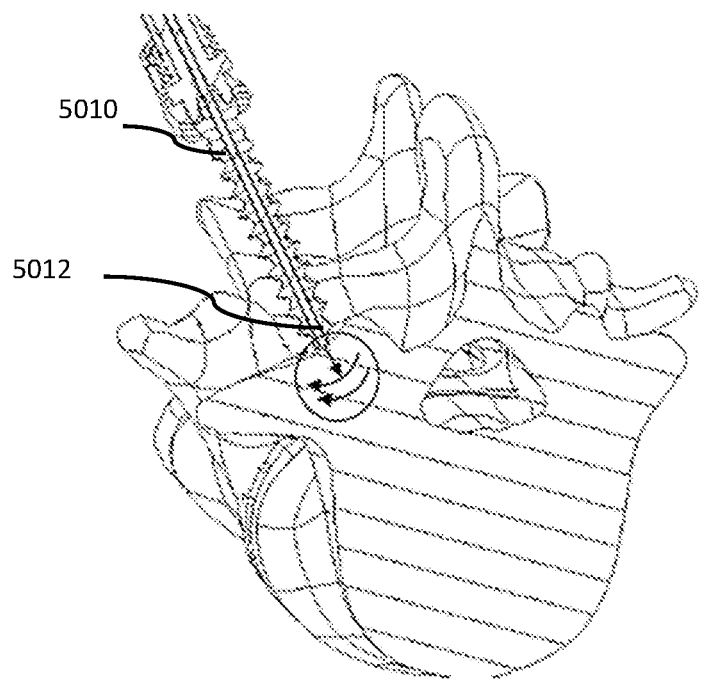
FIG. 57 is a cross-sectional view of the stylet and bone screw of the system of FIG. 55 at the bone interface.

As shown in FIG. 57, bone screw 5010 is positioned at or near the bone interface with the distal end of stylet 5150 substantially flush with distal end 5012 of bone screw 5010. Upon actuation of the energy source and thus excitation of the piezoelectric elements of transducer assembly 5275, ultrasonic vibrations are induced which oscillates stylet 5150 in a reciprocating longitudinal direction in strokes of about 20 to 100 micrometers ($\mu$m) which ultimately advances the stylet through distal end 5012 of bone screw 5010 and within the bone to create the pilot hole which is about 10 to 30 millimeters (mm) measured axially from the interface of the bone. Preferably, the stylet advances about 15 mm for creation of the pilot hole. Oscillation of stylet 5150 also occurs in a reciprocating torsional direction to twist and turn the stylet while it advances axially (shown by the arrows in FIG. 57).

After stylet 5150 is advanced to the desired depth, e.g. about 15 mm, stylet 5150 is simultaneously retracted via retraction assembly 5140 as bone screw 5010 is driven into the bone by screwdriver 5170. In this example, retraction assembly 5140 is positioned proximally of housing 5300 and defines passage 5123 for receiving stylet 5150 therethrough. Retraction assembly furthers includes an internally threaded portion for engaging threaded portion 5159 control device 5000 as described above in connection with control device 4120, stylet 5150 is rotationally coupled to screwdriver 5170 such that when screwdriver 5170 and thus stylet 5150 rotates in a clockwise manner, the engagement of threaded portion 5159 of stylet 5150 and internally threaded portion of retraction assembly 5140 causes proximal axial advancement of stylet 5150, e.g. retraction. Because the screwdriver is also rotating, this causes the bone screw 5010 to be driven into bone at the same time as stylet 5150 retracts. The pitch of the threads of threaded portion 5159 of stylet 5150 and the threads of bone screw 5010 may match to facilitate movement in opposite directions at the same rate.

Figure 58:
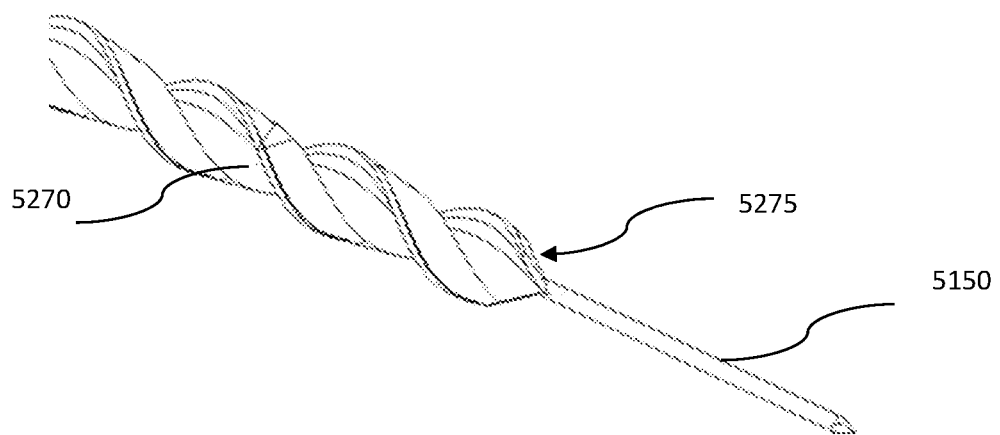
FIG. 58 is a perspective side view of a cannulated drill for use in conjunction with the control device of FIG. 55.

FIG. 58 shows drill 5270 which may alternatively be utilized in conjunction with control device 5000 rather than the screwdriver/bone screw, described in connection with FIGS. 55-57. Drill 5270 defines passage 5275 for receiving stylet 5150 therethrough. In this example, stylet 5150 is ultrasonically advanced through drill 5270 and into bone to create an initial pilot hole. The stylet is then retracted via retraction assembly 5140, and drill 5270 is advanced into bone.

FIG. 59 shows control device 6000 which is another embodiment of a device for advancing and retracting a stylet and is similar in most respects to control device 5000, the similar features of which will not be described again. Control device 6000 includes housing 6300 which operatively connects to a separate, non-integral ultrasound transducer device 6270 to impart the ultrasonic vibrations to advance the screwdriver or drill into bone.

Robotic systems may be used throughout the pre-operative and intra-operative stages of the surgery.

Preoperative planning for surgeries may include determining the bone quality in order to optimize bone preparation. Bone quality information, such as bone density or elastic modulus, can be ascertained from preoperative scans, e.g. CT scans. The bone quality data can be used to determine optimal properties for effective implant engagement. Examples of such methods are found in U.S. Pat. No. 10,166,109 to Ferko, filed on Sep. 18, 2014, entitled "Patient Specific Bone Preparation for Consistent Effective Fixation Feature Engagement," U.S. Patent Application Publication No. 2015/0119987 to Davignon et al., filed on Oct. 28, 2014, entitled "Implant Design Using Heterogeneous Bone Properties and Probabilistic Tools to Determine Optimal Geometries for Fixation Features," and U.S. Pat. No. 10,070,928 to Frank et al., filed on Jul. 1, 2015, entitled "Implant Placement Planning," each of which is hereby incorporated by reference herein in its entirety. In addition to preoperative imaging, robotic surgery techniques may employ imaging, such as fluoroscopy, during surgery. In such cases, systems integrating the surgical system with the imaging technologies facilitate flexible and efficient intraoperative imaging. Exemplary systems are described in U.S. Pat. No. 10,028,788 to Kang, filed on Dec. 31, 2013, entitled "System for Image-Based Robotic Surgery," hereby incorporated by reference herein in its entirety.

As in the instant case, robotic systems and methods may be used in the performance of spine surgeries to place implants in the patient's spine as in, for example, U.S. Patent Application Publication No. 2018/0325608 to Kang et al., filed on May 10, 2018, entitled "Robotic Spine Surgery System and Methods," the disclosure of which is hereby incorporated by reference herein in its entirety. The robotic system generally includes a manipulator and a navigation system to track a surgical tool relative to a patient's spine. The surgical tool may be manually and/or autonomously controlled. Examples of robotic systems and methods that employ both a manual and a semi-autonomous are described in U.S. Pat. No. 9,566,122 to Bowling et al., filed on Jun. 4, 2015, and entitled "Robotic System and Method for Transitioning Between Operating Modes," and U.S. Pat. No. 9,119,655 to Bowling et al., filed on Aug. 2, 2013, entitled "Surgical Manipulator Capable of Controlling a Surgical Instrument in Multiple Modes," each of which is hereby incorporated by reference herein in its entirety.

A robotic controller may be configured to control the robotic arm to provide haptic feedback to the user via the robotic arm. This haptic feedback helps to constrain or inhibit the surgeon from manually moving the screwdrivers 4170, 8170 of systems 4000, 8000 beyond predefined virtual boundaries associated with the surgical procedure. Such a haptic feedback system and associated haptic objects that define the virtual boundaries are described in, for example, U.S. Pat. No. 9,002,426 to Quaid et al., filed on Jun. 23, 2008, entitled "Haptic Guidance System and Method," and U.S. Pat. No. 8,010,180 to Quaid et al., filed on Dec. 21, 2012, entitled "Systems and Methods for Haptic Control of a Surgical Tool," and U.S. Pat. No. 10,098,704 to Bowling et al., filed on May 18, 2016, entitled "System and Method for Manipulating an Anatomy," each of which is hereby incorporated by reference herein in its entirety.

In some cases of autonomous positioning, a tool center point (TCP) of a surgical tool, such as screwdriver 4170, 8170, is brought to within a predefined distance of a starting point of a line haptic object that provides the desired trajectory. Once the tool center point is within the predefined distance of the starting point, actuation of an input causes the robotic arm to autonomously align and position the surgical tool on the desired trajectory. Once the surgical tool is in the desired position, the robotic system may effectively hold the rotational axis of the surgical tool on the desired trajectory by tracking movement of the patient and autonomously adjusting the robotic arm as needed to keep the rotational axis on the desired trajectory. Such teachings can be found in U.S. Patent Application Publication No. 2014/0180290 to Otto et al., filed on Dec. 21, 2012, entitled "Systems and Methods for Haptic Control of a Surgical Tool," which is hereby incorporated by reference herein in its entirety.

During operation of a robotic surgical system, the operation of the surgical tool can be modified based on comparing actual and commanded states of the tool relative to the surgical site is described in U.S. Patent Application Publication No. 2018/0168750 to Staunton et al., filed on Dec. 13, 2017, entitled Techniques for Modifying Tool Operation in a Surgical Robotic System Based on Comparing Actual and Commanded States of the Tool Relative to a Surgical Site," which is hereby incorporated by reference herein in its entirety. Further, robotic systems may be designed to respond to external forces applied to it during surgery, as described in U.S. Patent Application Publication No. 2017/0128136 to Post, filed on Nov. 3, 2016, entitled "Robotic System and Method for Backdriving the Same," which is hereby incorporated by reference herein in its entirety.

Further, because of the non-homogeneity of bone, applying a constant feed rate, a uniform tool path, and a constant rotational speed may not be efficient for all portions of bone. Systems and methods for controlling tools for such non-homogenous bone can be advantageous as described in U.S. Pat. No. 10,117,713 to Moctezuma de la Barrera et al., filed on Jun. 28, 2016, entitled "Robotic Systems and Methods for Controlling a Tool Removing Material From a Workpiece," which is hereby incorporated by reference herein in its entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stylet control system for selectively advancing and retracting a stylet comprising:
    a stylet having a first end and a second end, the second end being threaded;
    a screwdriver defining a bore for receiving a portion of the stylet and having a screw-engaging end for engaging a screw, the stylet being rotationally fixed relative to the screwdriver; and
    a control device having a passage for receiving the screwdriver and having an inner portion defining a lumen for receiving the portion of the stylet, the inner portion being threaded for engaging the threaded second end of the stylet;
    wherein the threaded second end of the stylet is configured to engage the threads of the inner portion of the control device to advance the stylet in a first axial direction when the control device is rotated while the screwdriver is prevented from rotating; and, the screwdriver is configured to advance the screw in the first axial direction and the stylet is configured to rotate such that the threaded second end of the stylet engages the threads of the inner portion and retracts in a second axial direction, opposite the first axial direction when the screwdriver is rotated in the first rotation direction and the control device is prevented from rotating.

2. The stylet control system of claim 1, wherein the stylet is keyed and the screwdriver includes a corresponding keyed feature on an inner surface to rotatably lock the stylet to the screwdriver.

3. The stylet control system of claim 1, further comprising a robotic end effector and a cap to couple the screwdriver to the robotic end effector.

4. The stylet control system of claim 1, wherein the control device is operatively connected to a robotic end effector.

5. The stylet control system of claim 1, wherein the control device further includes an ultrasonic transducer for imparting an ultrasonic force to the stylet.

6. The stylet control system of claim 5, wherein the ultrasonic transducer is positioned within a housing of the control device.

7. The stylet control system of claim 5, wherein the ultrasonic transducer is detachable from and external to a housing of the control device.

8. The stylet control system of claim 5, wherein the ultrasonic transducer includes piezoelectric material.

9. The stylet control system of claim 1, wherein the inner portion of the control device includes threaded pawls for engagement with the threads of the stylet.

10. A kit comprising:
the stylet control system of claim 1; and
a robotic end effector.

11. The kit of claim 10, further comprising a bone screw attachable to the screwdriver.

12. The kit of claim 10, wherein the control system includes an ultrasonic transducer for imparting an ultrasonic force to the stylet.

13. The kit of claim 11, wherein the bone screw is self-drilling.

14. The kit of claim 13, wherein the bone screw is cannulated.

15. A stylet control system for selectively advancing and retracting a stylet comprising:
a stylet having a first end and a second end;
a screwdriver defining a bore for receiving the stylet and having a screw-engaging end for engaging a screw, the stylet being rotationally fixed relative to the screwdriver;
a robotic end effector having a passage therethrough;
a cap configured to be received within a portion of the passage of the robotic end effector and being operatively connected to the screwdriver; and
a retraction feeder receivable within a lumen of the cap and having a mating engagement member for engaging the engagement member of the stylet;
wherein when the screwdriver is rotated in a first rotation direction, the screwdriver advances the screw in the first axial direction and the stylet engages the engagement member of the retraction feeder to retract the stylet in a second axial direction, opposite the first axial direction.

16. The stylet control system of claim 15, wherein the engagement members of the stylet and retraction feeders include mating threads, and the retraction feeder includes a threaded pawl for one-way engagement of the threaded stylet.

17. The stylet control system of claim 15, wherein the stylet is keyed and the screwdriver includes a corresponding keyed portion on an inner surface to rotatably lock the stylet to the screwdriver.

18. The stylet control system of claim 15, wherein the control system further includes an ultrasonic transducer for imparting an ultrasonic force to the stylet.

19. The stylet control system of claim 15, wherein the retraction feeder is rotatably locked within the end effector.

20. A stylet control system for selectively advancing and retracting a stylet comprising:
a stylet having a first end and a second end, the second end being threaded;
a screwdriver defining a bore for receiving the stylet and having a screw-engaging end for engaging a screw, the stylet being rotationally fixed relative to the screwdriver; and
a robotic end effector having a passage therethrough;
a cap configured to be received within a portion of the passage of the robotic end effector and being operatively connected to the screwdriver;
a retraction feeder receivable within a lumen of the cap and having a threaded pawl for one-way engagement with the threads of the second end of the stylet;
wherein when the screwdriver is rotated in a first rotation direction, the screwdriver advances the screw in the first axial direction and the threads of the stylet engages the threaded pawl of the retraction member to retract the stylet in a second axial direction, opposite the first axial direction.

* * * * *